United States Patent
Aslan

(10) Patent No.: US 9,243,017 B2
(45) Date of Patent: Jan. 26, 2016

(54) METAL-ASSISTED AND MICROWAVE-ACCELERATED EVAPORATIVE CRYSTALLIZATION

(71) Applicant: Morgan State University, Baltimore, MD (US)

(72) Inventor: Kadir Aslan, Baltimore, MD (US)

(73) Assignee: Morgan State University, Baltimore, MD (US)

(*) Notice: Subject to any disclaimer, the term of this patent is extended or adjusted under 35 U.S.C. 154(b) by 746 days.

(21) Appl. No.: 13/649,561

(22) Filed: Oct. 11, 2012

(65) Prior Publication Data

US 2013/0090459 A1    Apr. 11, 2013

Related U.S. Application Data

(60) Provisional application No. 61/545,808, filed on Oct. 11, 2011.

(51) Int. Cl.
| | |
|---|---|
| C30B 29/56 | (2006.01) |
| C07H 1/06 | (2006.01) |
| C07C 227/42 | (2006.01) |
| C30B 7/00 | (2006.01) |
| C30B 28/06 | (2006.01) |
| C30B 29/58 | (2006.01) |

(52) U.S. Cl.
CPC ............... C07H 1/06 (2013.01); C07C 227/42 (2013.01); C30B 7/005 (2013.01); C30B 28/06 (2013.01); C30B 29/58 (2013.01); C07B 2200/13 (2013.01)

(58) Field of Classification Search
CPC ........ C30B 29/54; C30B 29/29; C30B 29/65; C30B 7/02; C30B 7/14
See application file for complete search history.

(56) References Cited

U.S. PATENT DOCUMENTS

| 4,778,666 A | 10/1988 | Chu et al. |
| 2006/0213425 A1 | 9/2006 | Myerson et al. |

FOREIGN PATENT DOCUMENTS

| CN | 101857330 A | 10/2010 |
| WO | 02/29076 A1 | 4/2002 |

OTHER PUBLICATIONS

Communication dated Mar. 11, 2015 from the State Intellectual Property Office of the People's Republic of China in counterpart application No. 201280050176.7.

(Continued)

*Primary Examiner* — Robert M Kunemund
(74) *Attorney, Agent, or Firm* — Sughrue Mion, PLLC

(57) ABSTRACT

The present invention relates to methods for rapid crystallization of amino acids, drug molecules, proteins and DNA/peptides. One method for rapid crystallization of functional group-containing molecules selected from the group consisting of amino acids, drug molecules, proteins and DNA/peptides includes (A) providing at least one metal or metal oxide in particulate or thin film form to provide (a) selective nucleation sites for crystallization of the functional group-containing molecules due to interactions of their functional groups and metal surfaces or engineered metal surfaces and (b) a microwave-transparent medium to create a thermal gradient between the metal surfaces or engineered metal surfaces and a warmer solution containing functional group-containing molecules to be crystallized, and (B) conducting microwave heating to cause the functional group-containing molecules to be crystallized.

20 Claims, 22 Drawing Sheets
(22 of 22 Drawing Sheet(s) Filed in Color)

(56) References Cited

OTHER PUBLICATIONS

Li et al., "Study on Growth of α-Glycine Single Crystal and Rapid Crystallization Method," Journal of Synthetic Crystals, May 1995, vol. 24, No. 2, pp. 132-135 (4 pages total).
Wei et al., "A Study on the New Purification Method of Medicine Glycine α-Crystal," Chinese Journal of Medicinal Chemistry, Apr. 2001, vol. 11, No. 2, pp. 107-109 (3 pages total).
Mohammed et al., "New Tools in Biomedicine: iCrystal System and New Crystallization Platforms for Rapid Drug Development," IMPI's 48 Microwave Power Symposium, Jun. 2014, pp. 1-4 (4 total pages).
Grell et al., "Microwave-Accelerated Surface Modification of Plasmonic Gold Thin Films with Self-Assembled Monolayers of Alkanethiols," Langmuir, ACS Publications, 2013, vol. 29, pp. 13209-13216 (8 total pages).
Alabanza et al., "Crystallization of Amino Acids on a 21-well Circular PMMA Platform using Metal-Assisted and Microwave-Accelerated Evaporative Crystallization," Nano Biomed. Eng., 2013, vol. 5, No. 4, pp. 140-147 (8 total pages).
Grell et al.,"Rapid crystallization of glycine using metal-assisted and microwave-accelerated evaporative crystallization: the effect of engineered surfaces and sample volume," Nano Biomed. Eng., 2012, vol. 4, No. 3, pp. 125-131 (7 total pages).
Alabanza et al., "Rapid Crystallization of L-Alanine on Engineered Surfaces by Use of Metal-Assisted and Microwave-Accelerated Evaporative Crystallization," Crystal Growth and Design, ACS Publications, 2011, vol. 12, pp. 346-353 (8 total pages).
Mohammed et al., Rapid and Selective Crystallization of Acetaminophen using Metal-Assisted and Microwave-Accelerated Evaporative Crystallization, Nano Biomed. Eng., 2012, vol. 4, No. 1, pp. 35-40 (6 total pages).
Pinard et al., "Rapid crystallization of L-arginine acetate on engineered surfaces using metal-assisted and microwave-accelerated evaporative crystallization," The Royal Society of Chemistry, CrystEngComm, 2012, vol. 14, pp. 4557-4561 (5 total pages).
Mojibola et al.,"Crystal Engineering of L-Alanine with L-Leucine Additive using Metal-Assisted and Microwave-Accelerated Evaporative Crystallization," Crystal Growth and Design, ACS Publications, 2014, pp. A-H (8 total pages).
Alabanza et al., "Crystallization of L-alanine in the presence of additives on a circular PMMA platform designed for metal-assisted and microwave-accelerated evaporative crystallization," The Royal Society of Chemistry, CrystEngComm, 2012, vol. 14, pp. 8424-8431 (8 total pages).
International Search Report and Written Opinion for PCT/US12/59660 mail date Jan. 8, 2013.
Pinard et al.; Metal-Assisted and Microwave-Accelerated Evaporative Crystallization; Crystal Growth & Design, vol. 10, No. 11, 2010, pp. 4706-4709.
Lee et al.; Crystallization on Confined Engineered Surfaces: A Method to Control Crystal Size and Generate Different Polymorphs; J. Am. Chem. Soc. 9, vol. 127, No. 43, 2005 14983, Oct. 7, 2005, pp. 14982-14983.
Alabanza et al.; Metal-Assisted and Microwave-Accelerated Evaporative Crystallization: Application to L-Alanine; Crystal Growth & Design, vol. 11, No. 10, 2011, pp. 4300-4304.

Glass, RT, 3.2 M, pH = 6, 42 min

Glass, MW, 3.2 M, pH = 6, 33 sec

Glass – Room Temp    Glass – Microwave Power Level 1    Glass – Microwave Power Level 5    Glass – Microwave Power Level 10

SIF – Room Temp    SIF – Microwave Power Level 1    SIF – Microwave Power Level 5    SIF – Microwave Power Level 10

Glass_MW_PL1

SIF_MW_PL1

SIFs, RT, 3.2 M, pH= 6

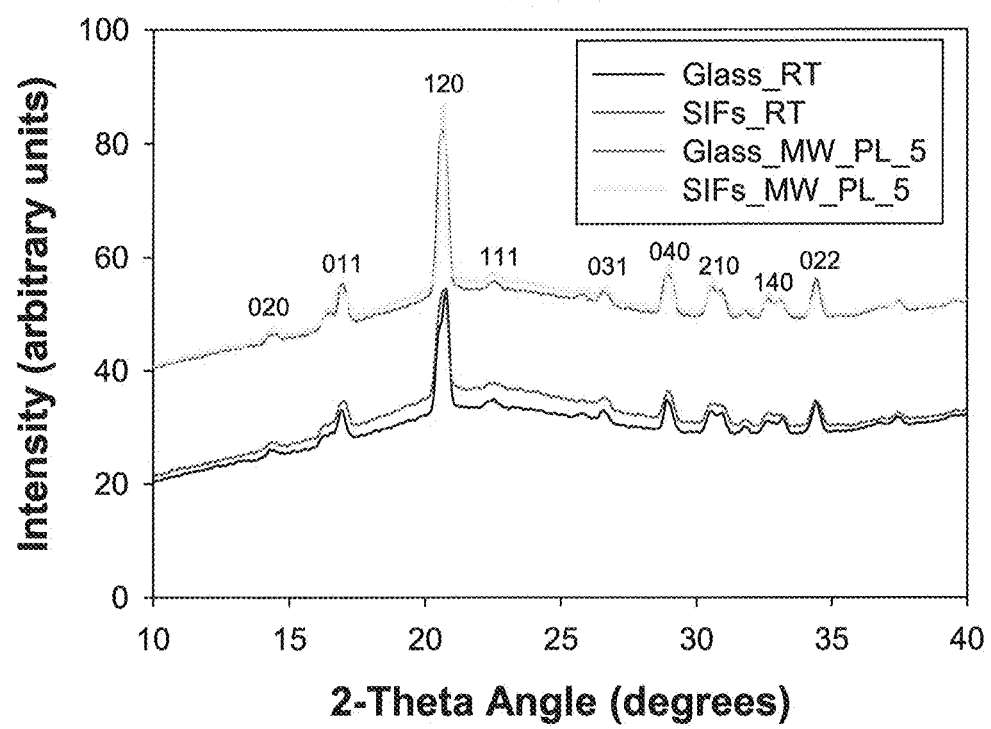

METAL-ASSISTED AND MICROWAVE-ACCELERATED EVAPORATIVE CRYSTALLIZATION

CROSS REFERENCE TO RELATED APPLICATION

This application claims priority from U.S. Provisional Application No. 61/545,808 filed Oct. 11, 2011, the disclosure of which is incorporated herein by reference.

FIELD OF THE INVENTION

The present invention relates to methods for rapid crystallization of amino acids, drug molecules, proteins and DNA/peptides using metal and metal oxides in particulate and thin film forms in combination with microwave heating (e.g., 0.3 to 30 GHz) using, e.g., a microwave power range of 1 W-30000 W. In particular, the present invention is directed to a platform technology, called metal-assisted and microwave-assisted evaporative crystallization (MA-MAEC), based on the combined use of (A) at least one metal or metal oxide in particulate or thin film form and (B) microwave heating for selective and rapid crystallization of small molecules. The MA-MAEC technique has the potential to selectively grow the desired polymorphs of small molecules "on-demand" in a fraction of the time as compared to the conventional evaporative crystallization.

BACKGROUND OF THE INVENTION

There has been an increased interest in the area of controlled crystal formation in the pharmaceutical industry; particularly in the area of crystal polymorphism and solid form purity (see Brittain, H. G., Effects of mechanical processing on phase composition. *Journal of Pharmaceutical Sciences* 2002, 91, (7), 1573-1580). Typically, the synthesized drugs are crystallized in the purest form possible and marketed in the forms of pills, tablets, etc.

In addition, crystallization is also used for understanding the molecular structures and interactions of proteins to develop new drug treatments that target specific human, animal, and plant diseases (see Roberts, M. M.; Heng, J. Y. Y.; Williams, D. R., Protein Crystallization by Forced Flow through Glass Capillaries: Enhanced Lysozyme Crystal Growth. *Crystal Growth & Design* 2010, 10, (3), 1074-1083).

In particular, crystallography has become a very useful tool for scientists in recent years due to its success in contributing to the understanding of molecular structures. While crystals of all molecular types are helping to recognize biological significances, proteins and amino acids are the primary molecules that are being focused on today. Amino acids are of particular importance because of their solubility and stabilizing properties that allow them to create multitudes of distinctive proteins (see Ito, L.; Kobayashi, T.; Shiraki, K.; Yamaguchi, H., Effect of amino acids and amino acid derivatives on crystallization of hemoglobin and ribonuclease A. *Journal of Synchrotron Radiation* 2008, 15, 316-318). Along with this, they also can serve as either intermediate or end products of biological functions, and have a wide range of applications in the chemical, food, cosmetic, and pharmaceutical industries (see Ng, K. M.; Harjo, B.; Wibowo, C., Development of amino acid crystallization processes: L-glutamic acid. *Industrial & Engineering Chemistry Research* 2007, 46, (9), 2814-2822).

One can find numerous studies related to crystallization of small molecules in the literature. For example, Myerson and co-workers have been employing polarized laser light irradiation for the crystallization of different polymorphs of glycine (see Garetz, B. A.; Matic, J.; Myerson, A. S., Polarization switching of crystal structure in the nonphotochemical light-induced nucleation of supersaturated aqueous glycine solutions. *Physical Review Letters* 2002, 89, (17), 175501). The same group also has demonstrated the use of self-assembled monolayers (SAMs) of alkane thiols on patterned gold thin films for size-controlled crystallization of glycine molecules through solvent evaporation (see Lee, A. Y.; Lee, I. S.; Dettet, S. S.; Boerner, J.; Myerson, A. S., Crystallization on confined engineered surfaces: A method to control crystal size and generate different polymorphs. *Journal of the American Chemical Society* 2005, 127, (43), 14982-14983). Ward and coworkers have employed nanoscale cylindrical pores to control the orientation of crystals formed by stereochemical inhibition (see Hamilton, B. D.; Weissbuch, I.; Lahav, M.; Hillmyer, M. A.; Ward, M. D., Manipulating Crystal Orientation in Nanoscale Cylindrical Pores by Stereochemical Inhibition. *Journal of the American Chemical Society* 2009, 131, (7), 2588-2596). Zukoski and co-workers have demonstrated the selective growth of γ-glycine crystals via concentrating micro-droplets of aqueous glycine solutions through slow evaporation-based crystallization platform (see He, G. W.; Bhamidi, V.; Wilson, S. R.; Tan, R. B. H.; Kenis, P. J. A.; Zukoski, C. F., Direct growth of gamma-glycine from neutral aqueous solutions by slow, evaporation-driven crystallization. *Crystal Growth & Design* 2006, 6, (8), 1746-1749).

In these reports, it was shown that the rapid evaporation of solvent produces the unstable β-form of glycine, while slowing the evaporation of solvent produced the kinetically stable α-form. Moreover, the generation of very slow super-saturation from water results in the stable γ-form (see He, G. W.; Bhamidi, V.; Wilson, S. R.; Tan, R. B. H.; Kenis, P. J. A.; Zukoski, C. F., Direct growth of gamma-glycine from neutral aqueous solutions by slow, evaporation-driven crystallization. *Crystal Growth & Design* 2006, 6, (8), 1746-1749). It was also shown that the distribution of glycine crystals can be affected by the surface (SAMs, polymers, etc.) as well as by the solution pH (see He, G. W.; Bhamidi, V.; Wilson, S. R.; Tan, R. B. H.; Kenis, P. J. A.; Zukoski, C. F., Direct growth of gamma-glycine from neutral aqueous solutions by slow, evaporation-driven crystallization. *Crystal Growth & Design* 2006, 6, (8), 1746-1749).

However, no techniques exist for the rapid (i.e., in a matter of seconds) and selective formation of crystals, e.g., the stable α- and γ-forms of glycine, without using additives, SAMs of alkane thiols or other engineered surfaces.

SUMMARY OF THE INVENTION

An object of the present invention is to provide a technique for the rapid and selective formation of crystals, e.g., the stable α- and γ-forms of glycine, without using additives, SAMs of alkane thiols or other engineered surfaces.

The above and other objects are achieved by the present invention, which includes the following embodiments.

1. A method for rapid crystallization of functional group-containing molecules selected from the group consisting of amino acids, drug molecules, proteins and DNA/peptides, the method comprising
    (A) providing at least one metal or metal oxide in particulate or thin film form to provide (a) selective nucleation sites for crystallization of the functional group-containing molecules due to interactions of their functional groups and metal surfaces or engineered metal surfaces and (b) a microwave-transparent medium to create a thermal gradient between the metal surfaces or engineered metal surfaces and a warmer solution containing functional group-containing molecules to be crystallized, and (B) conducting microwave heating to cause the functional group-containing molecules to be crystallized.

2. The method according to embodiment 1, wherein at least one metal or metal oxide in particulate or thin film form is silver, gold, copper, aluminum, zinc, chromium, palladium, nickel, rhodium, iron, platinum, tin, gallium, indium, cadmium, cobalt, manganese, ruthenium, or an oxide thereof.

3. The method according to embodiment 1, wherein at least one metal or metal oxide in particulate or thin film form is deposited onto a glass slide, polymeric material, paper or ceramic in a patterned fashion.

4. The method according to embodiment 1, wherein at least one metal or metal oxide in particulate or thin film form is deposited onto a glass slide, polymeric material, paper or ceramic in a random fashion.

5. The method according to embodiment 3, wherein the polymeric material is selected from the group consisting of polyamide, polycarbonate, polyester, polyetherimide, polyimide, polynitrocellulose, polyethylene, polypropylene, poly (ethylenevinylacetate), poly-2-pentene, polyphenylene oxide, polyphenylene sulfide, polysulfone, and polystyrene.

6. The method according to embodiment 4, wherein the polymeric material is selected from the group consisting of polyamide, polycarbonate, polyester, polyetherimide, polyimide, polynitrocellulose, polyethylene, polypropylene, poly (ethylenevinylacetate), poly-2-pentene, polyphenylene oxide, polyphenylene sulfide, polysulfone, and polystyrene.

7. The method according to embodiment 1, wherein the metal surfaces or engineered metal surfaces comprise a single metal or metal oxide.

8. The method according to embodiment 1, wherein the metal surfaces or engineered metal surfaces comprise any combination of metals or metal oxides.

9. The method according to embodiment 1, wherein at least one metal or metal oxide is in particulate form and has a particle size in a range of 2 nanometers to 2000 nanometers.

10. The method according to embodiment 1, wherein at least one metal or metal oxide is in thin film form and has a thin film thickness in a range of 10 nanometers to 2000 nanometers.

11. The method according to embodiment 1, further comprising metal surfaces modified with a) compounds containing i) amine or thiol head groups, ii) 3 to 16 methylene groups, and iii) functional end groups selected from the group consisting of amine, carboxyl, hydroxyl, and ethyl, or b) compounds containing i) amine or thiol head groups and ii) DNA or peptide or polynucleic acid or any single amino acid as functional end groups.

12. The method according to embodiment 1, wherein the microwave heating is at a microwave frequency selected from microwave frequencies of 0.3 to 30 GHz using a microwave power range of 1 W-30000 W.

13. The method according to embodiment 12, wherein the microwave frequency is 2.45 GHz.

14. The method according to embodiment 1, wherein the amino acids are selected from the group consisting of isoleucine, alanine, leucine, asparagine, lysine, aspartic acid, methionine, cysteine, phenylalanine, glutamic acid, threonine, glutamine, tryptophan, glycine, valine, proline, selenocysteine, serine, tyrosine, arginine, histidine, ornithine, and taurine.

15. The method according to embodiment 1, wherein the amino acids are selected from the group consisting of glycine, alanine, arginine, and glutamic acid.

16. The method according to embodiment 1, wherein the drug molecules are selected from the group consisting of acetaminophen and ranitidine.

17. The method according to embodiment 1, wherein the proteins are selected from the group consisting of proteins found in humans and animals at their healthy and diseased states.

18. The method according to embodiment 1, wherein the DNA and peptides are selected from the group consisting of DNA and peptides found in humans and animals at their healthy and diseased states.

19. The method according to embodiment 1, wherein the functional groups are selected from the group consisting of amine, thiol, ethyl, and hydroxyl.

20. The method according to embodiment 1, wherein the metal surfaces or engineered metal surfaces remain at room temperature after microwave heating.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 29 shows a powder X-ray diffraction pattern of L-alanine crystals.

DETAILED DESCRIPTION OF THE INVENTION

Figure 1:
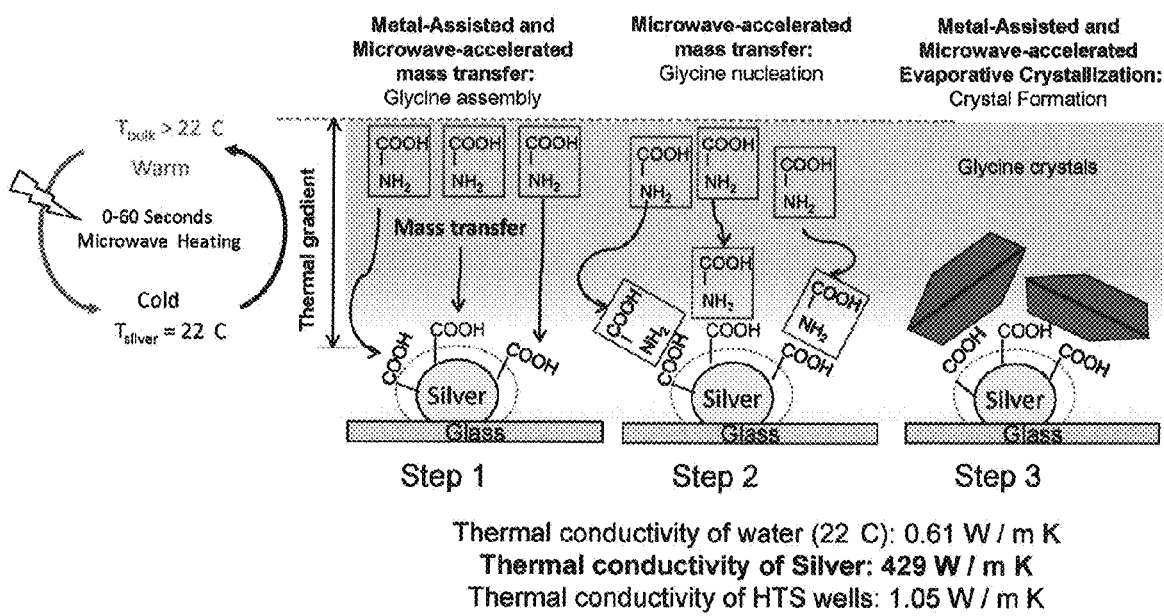
FIG. 1 is a schematic depiction of Metal-Assisted and Microwave-Accelerated Evaporative Crystallization.

Any metal or metal oxide can be used in the present invention. Preferred metals and metal oxides are silver, gold, copper, aluminum, zinc, chromium, palladium, nickel, rhodium, iron, platinum, tin, gallium, indium, cadmium, cobalt, manganese, ruthenium, and oxides thereof.

In one embodiment of the present invention, these metals and metals oxides can be used alone.

In another embodiment of the present invention, two or more of these metals and metal oxides can be used at the same time.

Any suitable particle size can be used for the metal and metal oxide particles. A preferred particle size range for the metal and metal oxide particles is 2 nanometers to 2000 nanometers.

Any suitable film thickness can be used for the metal and metal oxide thin films. A preferred thin film thickness range for the metal and metal oxide thin films is 10 nanometers to 2000 nanometers.

Surface engineering includes the modification of metal and metal oxides with

A) compounds containing i) amine or thiol head groups, ii) 3 to 16 methylene groups, and iii) functional end groups (amine, carboxyl, hydroxyl, ethyl), or B) compounds containing i) amine or thiol head groups, and ii) DNA or peptide or polynucleic acid or any single amino acids as functional end groups.

Any suitable microwave frequency can be used. A preferred microwave frequency ranges from 0.3 to 30 GHz. A particularly preferred microwave frequency is 2.45 GHz.

Any suitable microwave power can be used. A preferred microwave power range is 1 W-30000 W. A particularly preferred microwave range is 1 W-1200 W.

Amino acids which can be used in the present invention are isoleucine, alanine, leucine, asparagine, lysine, aspartic acid, methionine, cysteine, phenylalanine, glutamic acid, threonine, glutamine, tryptophan, glycine, valine, proline, selenocysteine, serine, tyrosine, arginine, histidine, ornithine, and taurine. Preferred amino acids include glycine, alanine, arginine, and glutamic acid.

Drug molecules which can be used in the present invention include all commercially available drug molecules and future molecules synthesized using organic chemistry and drug molecules derived from living organisms including bacteria and plants living on land and in the seas. Preferred drug molecules include acetaminophen and ranitidine.

Proteins which can be used in the present invention include all proteins found in humans and animals at their healthy and diseased states.

DNA/peptides which can be used in the present invention include all DNA/peptides found in humans and animals at their healthy and diseased states.

Any suitable solvent can be used for the amino acids, drug molecules, proteins, and DNA/peptides. A preferred solvent is deionized water or double-distilled water.

The present invention provides rapid crystallization of amino acids, drug molecules, proteins and DNA/peptides. In this regard, crystallization is achieved in less than 180 seconds for samples smaller than 200 microliters in the case of amino acids and drug molecules such as in embodiments 14, 15 and 16 above, and crystallization is achieved in less than 2 hours for samples smaller than 200 microliters in the case of proteins and DNA/peptides such as in embodiments 17 and 18.

The present invention will now be described in further detail by way of the following examples, which should not be considered as limiting the present invention in any way. In the examples, power level 1, 5 and 10 means the application of 900 W in 10%, 50% and 100% of the total time, respectively.

Example 1

The MA-MAEC technique was tested with a model amino acid, i.e., glycine. Glycine has three distinct polymorphs at ambient conditions: α, β and γ (see Lee, A. Y.; Lee, I. S.; Dettet, S. S.; Boerner, J.; Myerson, A. S., Crystallization on confined engineered surfaces: A method to control crystal size and generate different polymorphs. *Journal of the American Chemical Society* 2005, 127, (43), 14982-14983). The formation of glycine crystals mainly depends on the type of solvent, pH and concentration. In the MA-MAEC technique used in this example, metal nanostructures serves as 1) selective nucleation sites for the crystallization of glycine due to the interactions of primary amine (of glycine) and silver nanostructures and 2) a microwave-transparent medium for the creation of thermal gradient between a warmer solution and the silver nanostructures that remain at room temperature after microwave heating (see Aslan, K.; Geddes, C. D., Microwave-accelerated metal-enhanced fluorescence: Platform technology for ultrafast and ultrabright assays. *Analytical Chemistry* 2005, 77, (24), 8057-8067). The microwave heating allows for the significant reduction in the time of crystallization process.

FIG. 1 depicts the proposed mechanism for the MA-MAEC technique. In MA-MAEC, upon exposure to microwave heating, a thermal gradient is created between the solution and the silver nanoparticles due to ~620-fold difference in the thermal conductivity of silver (429 W/m K) and water (0.61 W/m K). This thermal gradient allows for the mass transfer of glycine molecules from the warmer solution to the cooler nanoparticles in an effort to thermally equilibrate the system. Subsequently, glycine molecules assemble either directly (or by other functional groups on silver) onto the silver nanoparticles (FIG. 1, step 1). With continued microwave heating, mass transfer of glycine continues and the glycine molecules assemble onto the ones on the surface of silver nanoparticles in a process called nucleation (FIG. 1, step 2). Crystal growth takes place as the solution evaporates and subsequent glycine molecules assemble on to one another until all glycine molecules crystallize (FIG. 1, step 3).

Silver island films (SIFs) were deposited onto glass microscope slides by allowing them to soak in a heated silver nitrate/D-glucose solution as previously described (see Aslan, K.; Geddes, C. D., Microwave-accelerated metal-enhanced fluorescence: Platform technology for ultrafast and ultrabright assays. *Analytical Chemistry* 2005, 77, (24), 8057-8067). Freshly prepared SIFs (FIG. 9) were used in all the experiments. The effect of concentration and pH on the crystallization of glycine in deionized water (no other solvent was used) at constant solution volume was studied. In this regard, aqueous solutions of glycine (>99.5%, Sigma-Aldrich, USA) with three different concentrations were prepared: 1.60, 3.20 and 4.0 M. The pH of the glycine solutions was adjusted to 4 (acidic), 6 (neutral) and 9 (basic) using 6M HCl or 6M NaOH. In the MA-MAEC experiments, a fixed volume (20 μl) of freshly prepared glycine solution was pipetted onto SIFs-coated glass slides, which were then either heated in a conventional microwave oven (100% power level) or incubated at room temperature. The time taken for the solution to completely evaporate was recorded. In two control samples, the crystallization of glycine was carried out on blank glass slides with microwave heating and on blank glass slides at room temperature.

Glycine crystals formed on SIFs and glass slides were characterized by microscopy (optical microscope and scanning electron microscope, FIGS. 10-17) and powder X-Ray Diffraction (XRD) (see the Supporting Information below for the discussion of X-ray crystallography data). The crystal polymorph distribution was calculated using the microscope images of three different samples. Table 1 below summarizes the results for the crystallization of glycine using the MA-MAEC technique and control experiments. In this regard, the crystal morphology, crystal polymorph distribution (i.e., purity) and the total time to evaporate different glycine solutions are listed.

TABLE 1

Summary of results for the crystallization of glycine using MA-MAEC technique and control experiments.

| | SIFs- Microwave Crystal morphology/(purity)/time CONCENTRATION | | | SIFs-Room Temperature Crystal morphology/(purity)/time CONCENTRATION | | |
|---|---|---|---|---|---|---|
| pH | 1.6M | 3.2M | 4.0M | 1.6M | 3.2M | 4.0M |
| 4 | N/A[#] — 43 ± 6 sec | α, γ (10:90%) 24 ± 5 sec | — N/A[#] 22 ± 3 sec | α, γ (10:90%) 12 ± 0 min | α, γ (60:40%) 10 ± 0 min | γ (100%) 10 ± 0 min |
| 6 | α (100%) 57 ± 6 sec | α (100%) 40 ± 1 sec | α, γ (25:35%) 50 ± 1 sec | α, γ (70:30%) 25 ± 0 min | α (100%) 13 ± 1 min | α (100%) 11 ± 0 min |
| 9 | γ, β (70; 30%) 53 ± 6 sec | α, γ, β (30; 40; 30%) 30 ± 1 sec | γ (100%) 30 ± 1 sec | α, γ, β (15; 60; 25%) 24 ± 2 min | α, γ (5:95%) 21 + 1 min | γ, β (ND*) 17 ± 0 min |

| | Glass (No silver)-Microwave Crystal morphology/(purity)/time CONCENTRATION | | | Glass (No silver)-Room Temperature Crystal morphology/(purity)/time CONCENTRATION | | |
|---|---|---|---|---|---|---|
| pH | 1.6M | 3.2M | 4.0M | 1.6M | 3.2M | 4.0M |
| 4 | N/A[#] — 55 ± 6 sec | N/A[#] — 27 ± 6 sec | — ND* 20 ± 1 sec | γ (100%) 60 ± 0 min | γ (100%) 40 ± 0 min | γ (100%) 20 ± 0 min |
| 6 | α, γ (5:95%) 48 ± 3 sec | α, γ (50:50%) 33 ± 3 sec | — ND* 29 ± 1 sec | α, γ (10:90%) 46 ± 0 min | α, γ (50:50%) 42 ± 0 min | α, γ, β (5; 35; 60%) 12 ± 0 min |
| 9 | γ (100%) 32 ± 3 sec | N/A[#] — 21 ± 2 sec | — ND* 28 ± 2 sec | α, γ (10:90%) 40 ± 0 min | — ND* 40 ± 0 min | α, γ, β (35; 35; 30%) 13 ± 0 min |

[#]No crystals;
*% Not Determined;
Average of 3 samples

Figure 2:
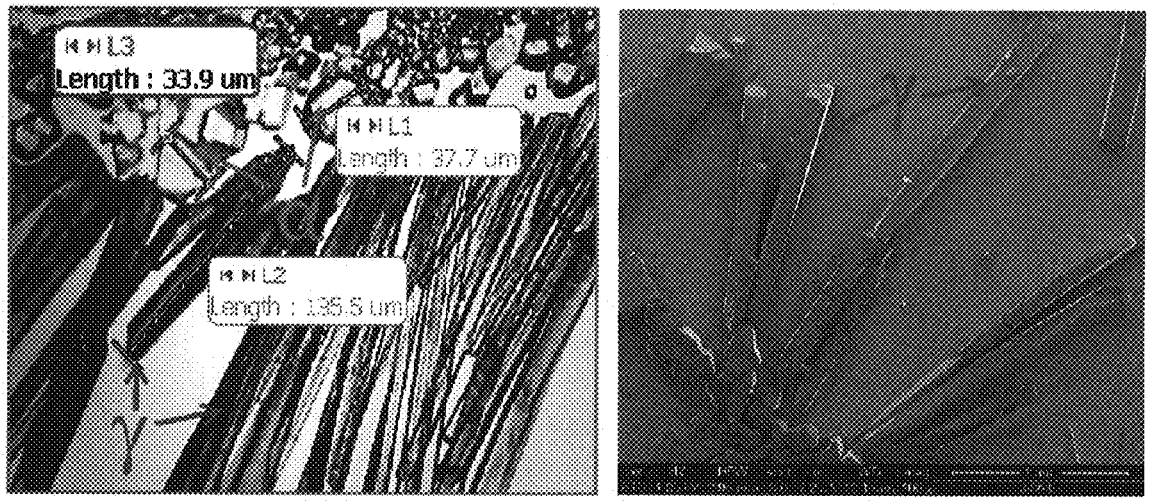
FIG. 2 shows optical and SEM images for glycine crystals grown on blank glass slides from 3.2M solution, pH=6 (Top) at room temperature and (Bottom) using microwave heating (MW), wherein * indicates plate-like α-glycine.
Figure 2:
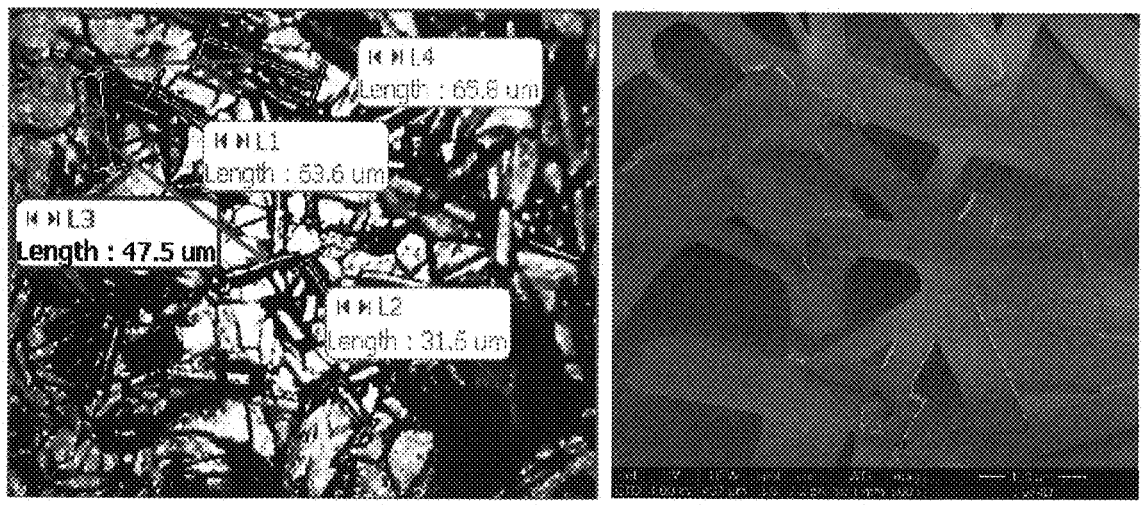

For a fixed volume of glycine solution, the total evaporation time on blank glass slides at room temperature (a control sample, evaporative crystallization) was recorded to be between 12 (for 4M, pH=6) and 60 minutes (for 1.6M, pH=4). As the concentration of glycine solution is increased the total time of crystallization was decreased up to 4-fold, which is due to the presence of more glycine molecules in solution, driving the crystallization process more rapidly. In acidic and basic conditions, γ-form of glycine was dominant. α-form of glycine was observed mostly at pH=6 as confirmed by XRD. FIGS. 2—Top and 10 show the optical microscope and SEM images of the glycine crystals formed on blank glass slides at room temperature. As expected, γ-glycine is formed as needles (130-200 μm in length) and α-glycine (5-40 μm in length) is formed as bipyramids, which can be explained by a kinetically controlled process involving the presence of cyclic dimmers (see Weissbuch, I.; Lahav, M.; Leiserowitz, L., Toward stereochentical control, monitoring, and understanding of crystal nucleation. *Crystal Growth & Design* 2003, 3, (2), 125-150).

When identical glycine solutions on blank glass slides were exposed to microwave heating, glycine the solution completely evaporated in 20-55 seconds. However, glycine crystals were grown only for three out of nine solutions and the crystals were not well organized as compared to those grown at room temperature. That is, microwave heating of glycine solution on blank glass slides did not yield better crystals (FIG. 2—Bottom, FIG. 11, and FIG. 18B.

Figure 3:
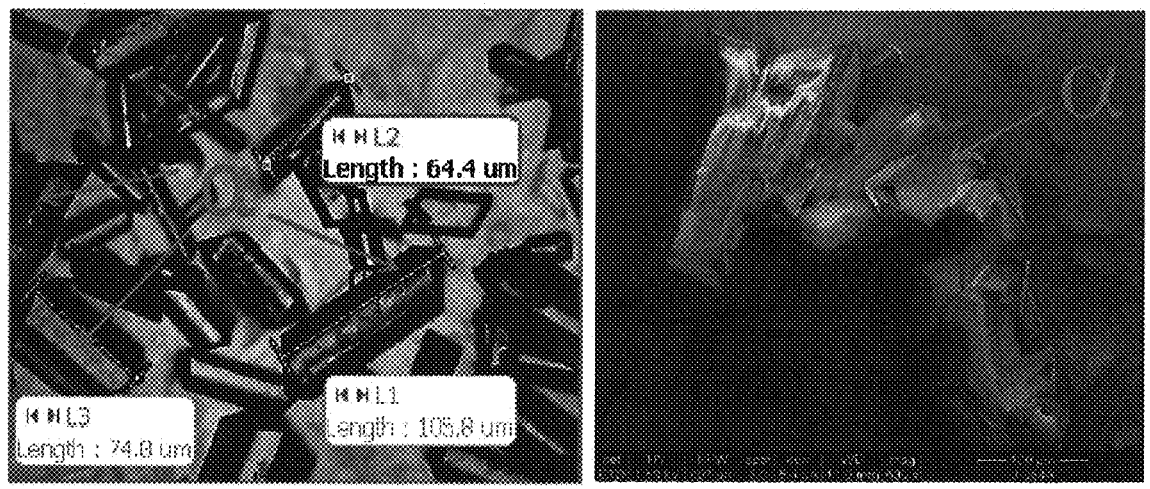
FIG. 3 shows optical and SEM images for glycine crystals grown on SIFs from 3.2M solution, pH=6 (Top) at room temperature and (Bottom) using microwave heating.
Figure 3:
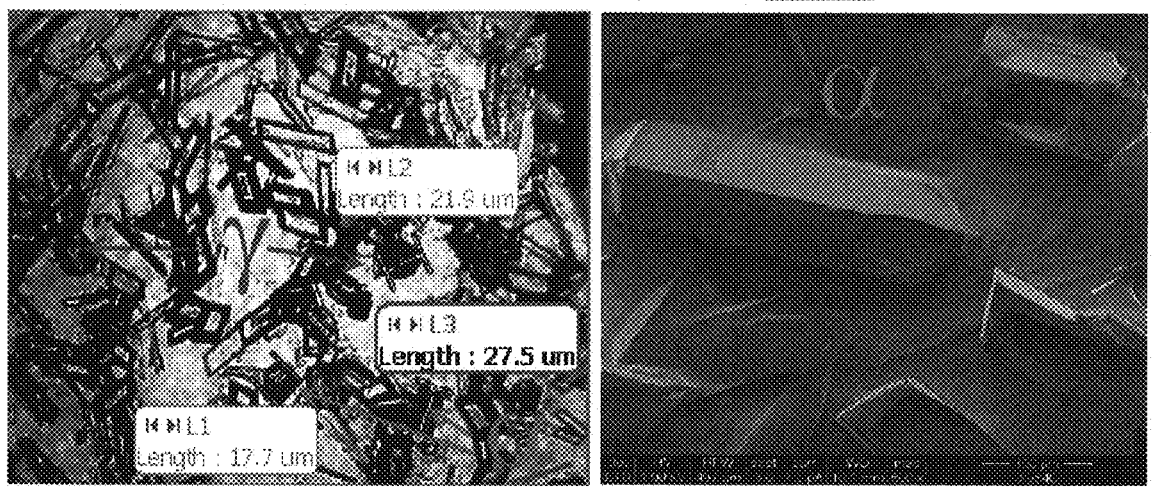

Since primary amine (and thiol) groups have affinity towards silver nanostructures, glycine molecules are expected to assemble onto silver nanostructures through amine groups facing the silver surface. That is, silver nanostructures serve as selective nucleation sites for the crystallization of glycine, which increases the rate of crystallization and potentially result in selective polymorphism. Subsequently, the growth of glycine crystals at room temperature was carried out on SIFs. For a fixed volume of glycine solution, the total evaporation time on SIFs at room temperature was reduced by up to 5-fold (for 1.6 M, pH=4) as compared to those on blank glass slides at room temperature. Moreover, glycine crystals were grown on SIFs for all nine conditions and these crystals are well organized and larger (FIG. 3—Top and FIGS. 12-14) as compared to those grown on blank glass slides. In this regard, the size of α-glycine grown on SIFs (up to ~100 μm in size) are ~2-fold larger than those grown on blank glass slides. This is thought to be due to the presence of multiple silver nanostructures within close proximity to one another (FIG. 9), which affords for multiple crystal nucleation/growth processes to occur simultaneously.

It is also important to note that γ-glycine grown on SIFs reach lengths >1 mm (FIG. 13), which makes them a very promising candidate for non-linear optical applications (see Bhat, M. N.; Dharmaprakash, S. M., Effect of solvents on the growth morphology and physical characteristics of nonlinear optical gamma-glycine crystals. *Journal of Crystal Growth* 2002, 242, (1-2), 245-252). In addition, a superior distribution of crystal polymorphs was observed on SIFs, where a desired type of polymorph can be grown in a relatively short time. These observations prove that the use of silver nanostructures (Metal-Assisted Crystallization, MAC) can significantly improve the crystallization process.

Despite the notable improvements afforded by MAC, the crystallization process (for complete evaporation of a 20 μl solution) still requires up to 25 minutes to be completed. Subsequently, the effect of microwave heating on the crystallization process on SIFs was investigated (i.e., MA-MAEC). When identical glycine solutions on SIFs were exposed to microwave heating, the glycine solution completely evaporated in 22-57 seconds (up to ~60-fold decrease as compared to glass at room temperature). Seven (out of 9) of the glycine solutions yielded well organized glycine crystals (FIG. 3—Bottom and FIGS. 15-17). In MA-MAEC the heating of glycine solutions to higher temperatures (water is completely evaporated) resulted in the transformation of γ-form into α- and β-forms. This is due to the fact that α- and γ-glycine are enantiotropically related and such transformation occurs at high temperatures (see Lee, A. Y.; Lee, I. S.; Dettet, S. S.; Boerner, J.; Myerson, A. S., Crystallization on confined engineered surfaces: A method to control crystal size and generate different polymorphs. *Journal of the American Chemical Society* 2005, 127, (43), 14982-14983). The existence of the high energy β-form can be explained by the high supersaturation process resulted by rapid evaporation of water (see Lee, A. Y.; Lee, I. S.; Dettet, S. S.; Boerner, J.; Myerson, A. S., Crystallization on confined engineered surfaces: A method to control crystal size and generate different polymorphs. *Journal of the American Chemical Society* 2005, 127, (43), 14982-14983).

It is important to note that glycine crystals started to appear on SIFs before the complete evaporation (<1 min) of the aqueous glycine solution. That is, one can use the MA-MAEC technique without complete evaporation of the solvent, especially for the separation of impurities from the desired crystals.

In summary, the proof-of-principle of a platform technology, which involves the use of silver nanostructures with and without microwave heating to significantly improve the crystallization of organic small molecules, was demonstrated. In this regard, the crystallization of a model organic molecule (glycine) from a small volume aqueous solution using microwave heating was achieved in seconds. Glycine crystals grown on silver nanostructures with and without microwave heating were found be larger than those grown on blank glass slides. The MA-MAEC technique has the potential to selectively grow the desired polymorphs of small organic and biological molecules "on-demand" in a fraction of the time as compared to the conventional evaporative crystallization.

Supporting Information: The additional images of glycine crystals (Supporting Information 1) and powder XRD data (Supporting Information 2) are discussed below.

Figure 9:
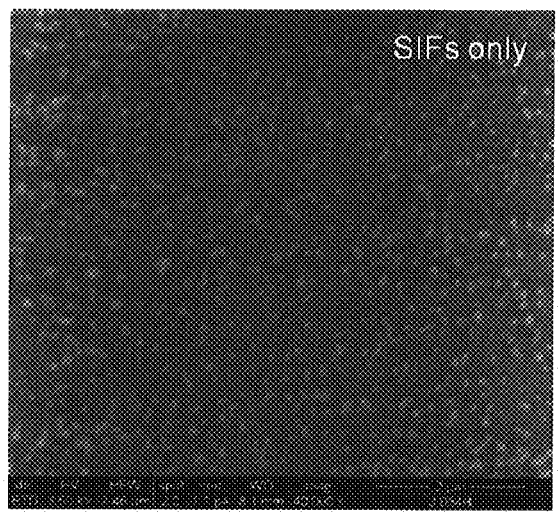
FIG. 9 shows an SEM image of Silver Island Films (SIFs) on blank glass slides. SIF's are ~80 nm in diameter.

Supporting Information 1:

FIG. 9 shows an SEM image of Silver Island Films (SIFs) on blank glass slides. SIF's are ~80 nm in diameter.

Figure 10:
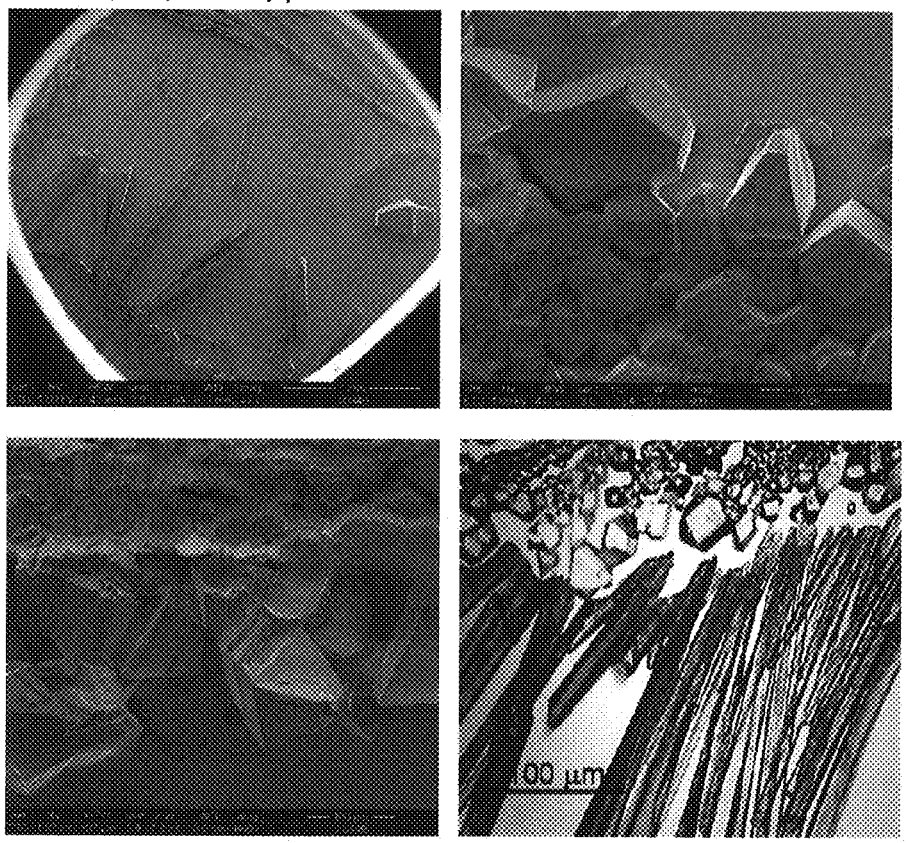
FIG. 10 shows SEM and optical images of glycine crystals grown from 3.2 M pH=6 aqueous glycine solution on blank glass slides at room temperature (RT).

FIG. 10 shows SEM and optical images of glycine crystals grown from 3.2 M pH=6 aqueous glycine solution on blank glass slides at room temperature (RT).

Figure 11:
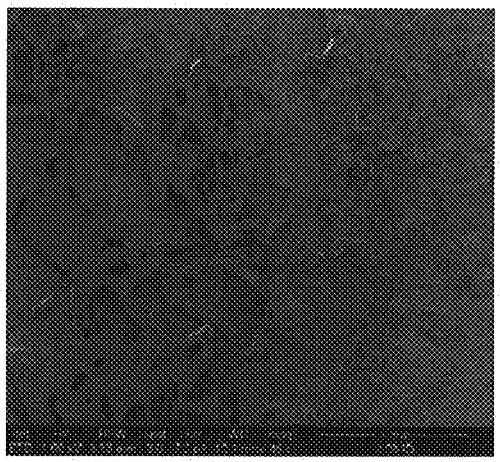
FIG. 11 shows SEM and optical images of glycine crystals grown from various aqueous glycine solutions on blank glass slides using microwave heating (MW).
Figure 11:
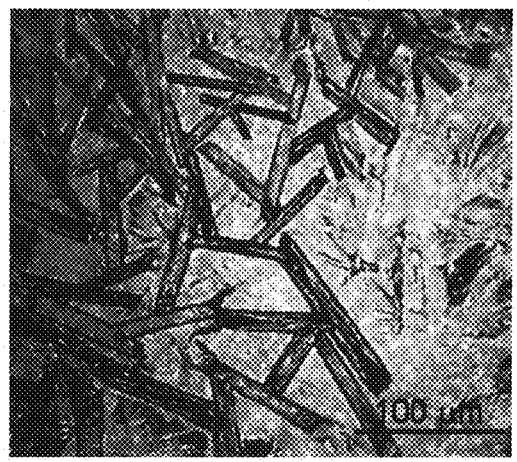
Figure 11:
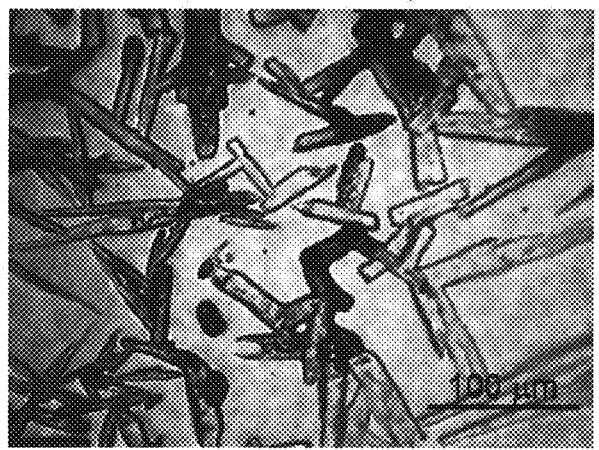

FIG. 11 shows SEM and optical images of glycine crystals grown from various aqueous glycine solutions on blank glass slides using microwave heating (MW).

Figure 12:
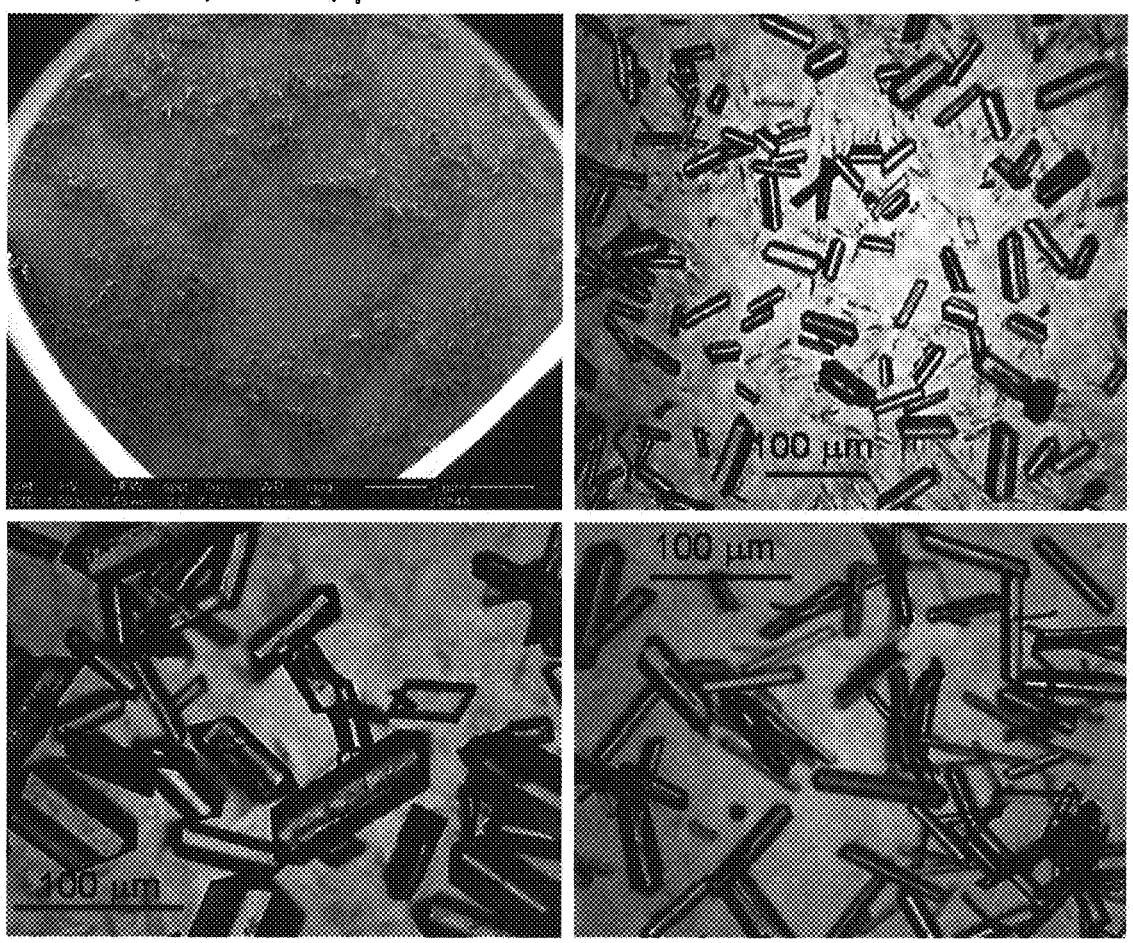
FIG. 12 shows SEM and optical images of glycine crystals grown from 3.2 M pH=6 aqueous glycine solution on SIFs at room temperature (RT).

FIG. 12 shows SEM and optical images of glycine crystals grown from 3.2 M pH=6 aqueous glycine solution on SIFs at room temperature (RT).

Figure 13:
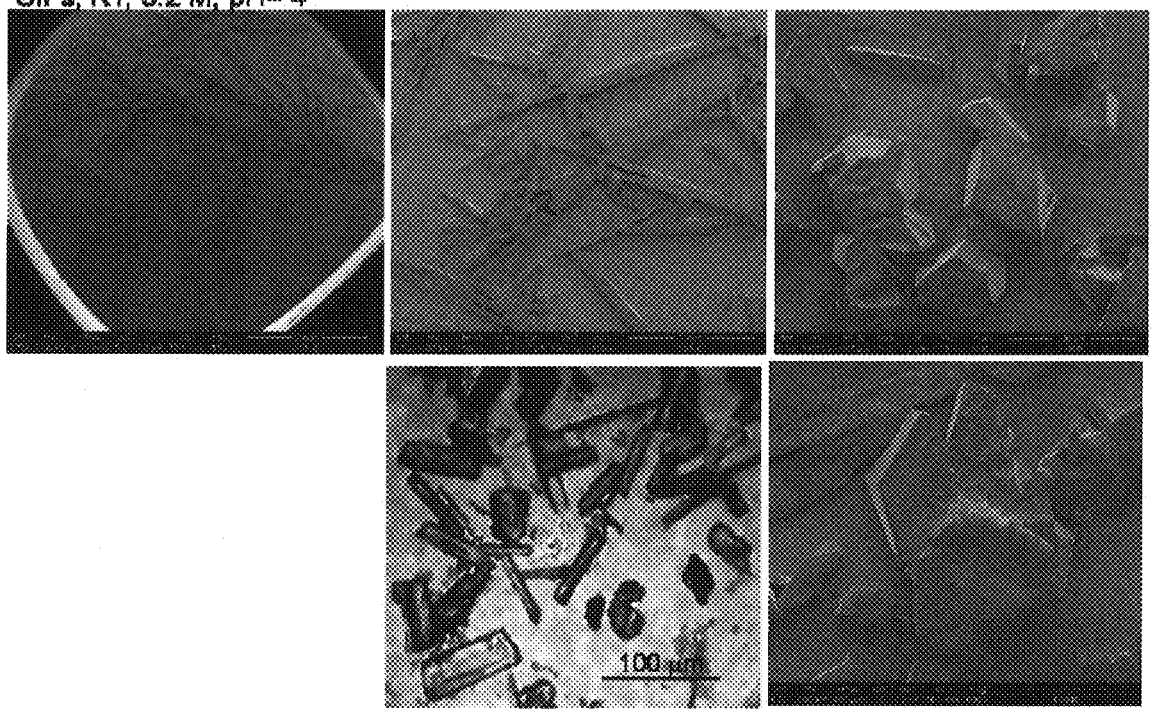
FIG. 13 shows SEM and optical images of glycine crystals grown from 3.2 M pH=4 aqueous glycine solution on SIFs at room temperature (RT).

FIG. 13 shows SEM and optical images of glycine crystals grown from 3.2 M pH=4 aqueous glycine solution on SIFs at room temperature (RT).

Figure 14:
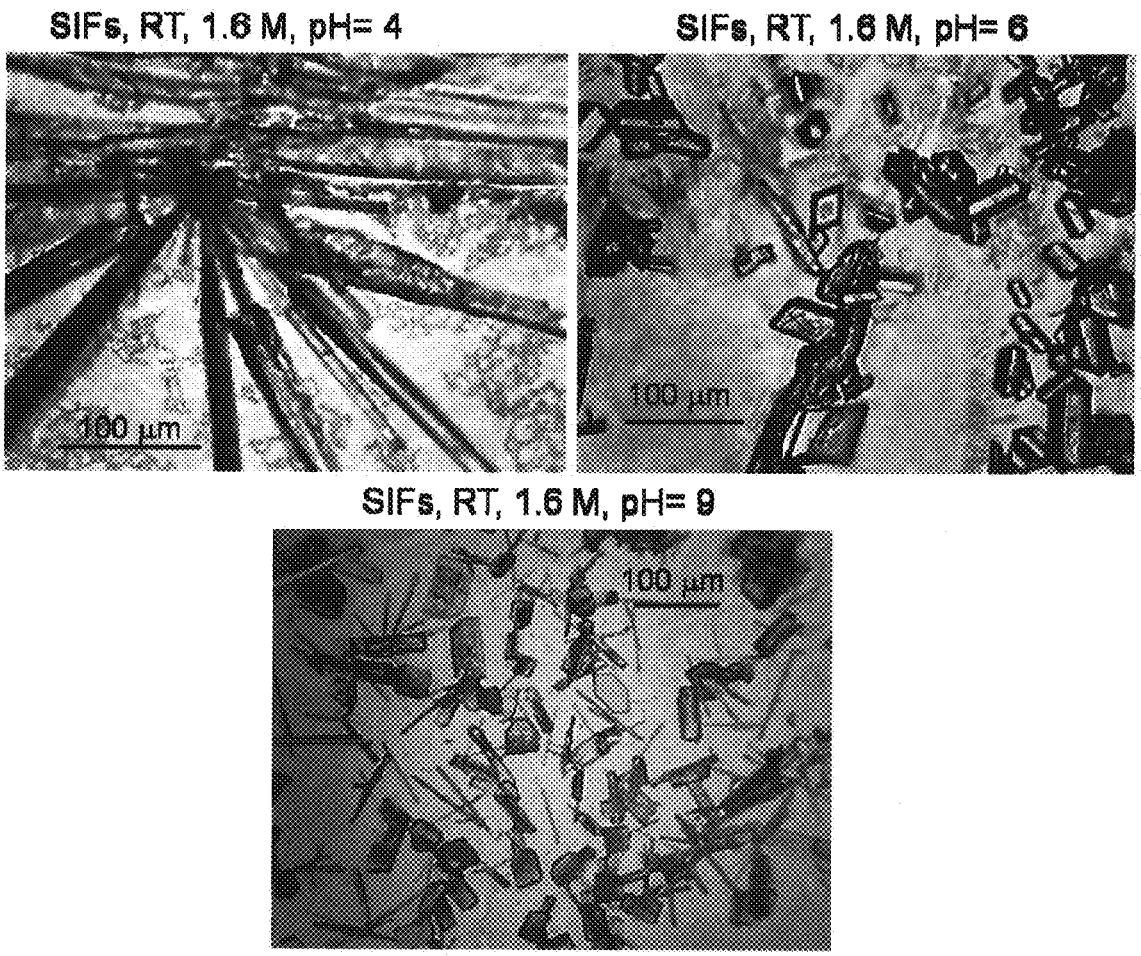
FIG. 14 shows optical microscope images of glycine crystals grown from various aqueous glycine solutions on SIFs at room temperature (RT).

FIG. 14 shows optical microscope images of glycine crystals grown from various aqueous glycine solutions on SIFs at room temperature (RT).

Figure 15:
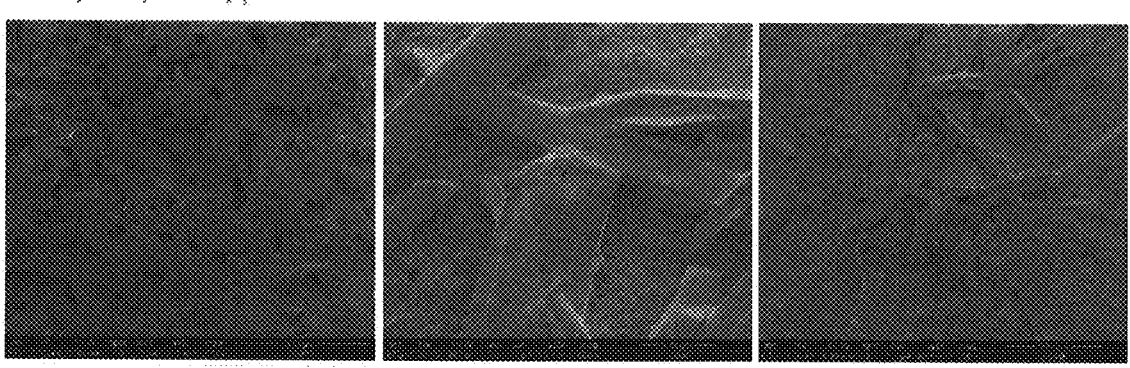
FIG. 15 shows SEM images of glycine crystals grown from 3.2 M pH=4 aqueous glycine solution on SIFs using microwave heating (MW).

FIG. 15 shows SEM images of glycine crystals grown from 3.2 M pH=4 aqueous glycine solution on SIFs using microwave heating (MW).

Figure 16:
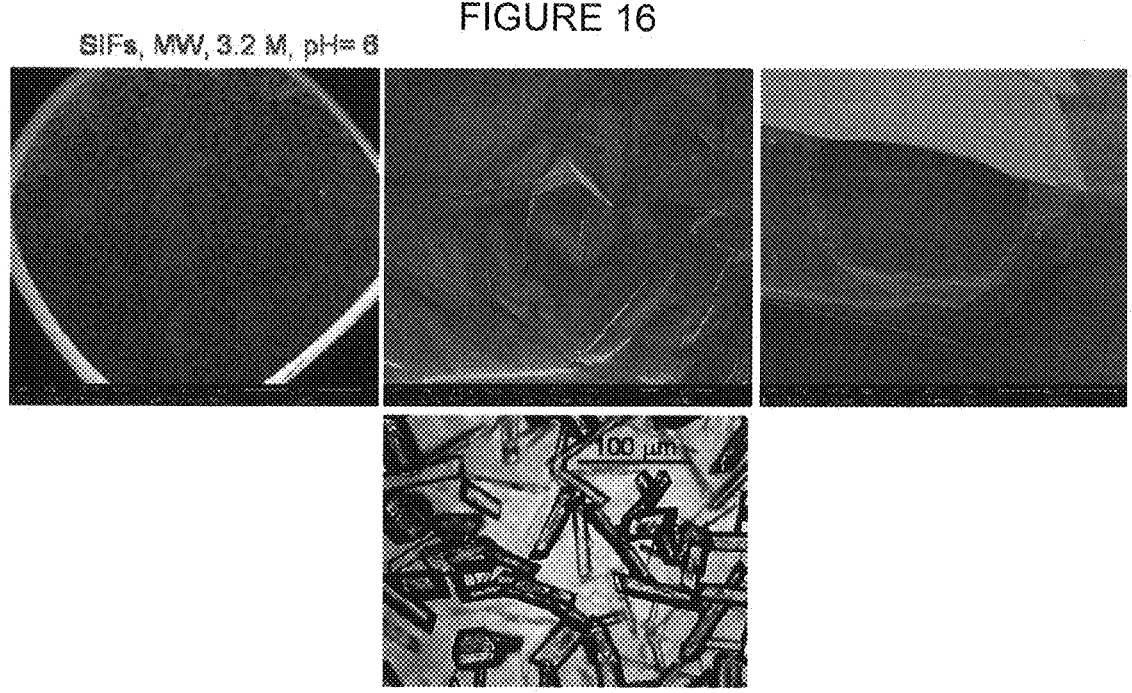
FIG. 16 shows SEM and optical images of glycine crystals grown from 3.2 M pH=6 aqueous glycine solution on SIFs using microwave heating (MW).

FIG. 16 shows SEM and optical images of glycine crystals grown from 3.2 M pH=6 aqueous glycine solution on SIFs using microwave heating (MW).

Figure 17:
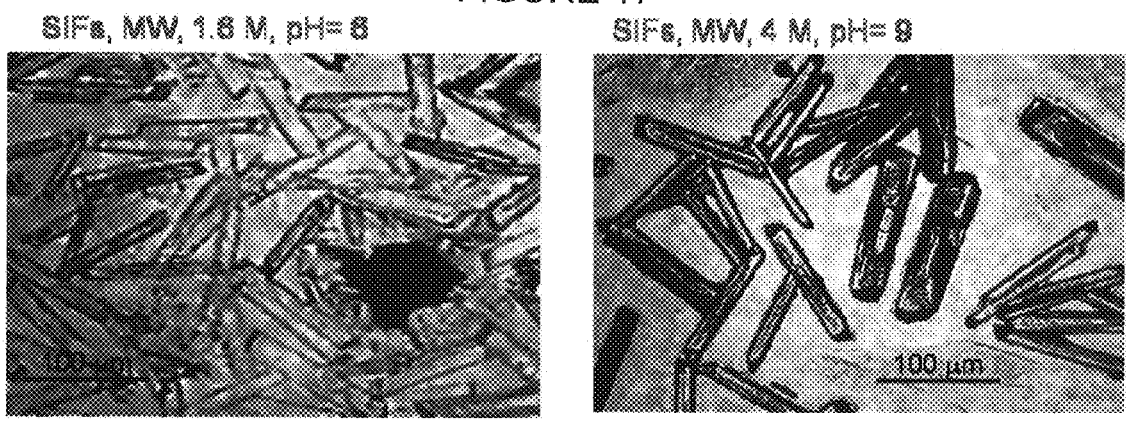
FIG. 17 shows optical microscope images of glycine crystals grown from various aqueous glycine solutions on SIFs using microwave heating (MW).

FIG. 17 shows optical microscope images of glycine crystals grown from various aqueous glycine solutions on SIFs using microwave heating (MW).

Supporting Information 2:

Characterization of glycine crystals with powder X-ray diffraction (XRD) was as follows. XRD data for glycine crystals placed in a capillary tube with thin walls (0.02 mm) were collected using an in-house X-ray generator (MicroMax 7, Rigaku/MSC, The Woodlands, Tex.) and a Raxis4++ image plate detector (Rigaku/MSC), which is housed at the Core Facilities of the Department of Pharmaceutical Sciences, University of Maryland School of Pharmacy. The distance between the detector and samples were kept constant at 75 mm. The radiation source was CuK$\alpha$ (wavelength: 0.54 nm). The 2-D XRD data was collected at $0° \leq \delta \leq 120°$ at values of $0° \leq 2\theta \leq 40°$.

Figure 20:
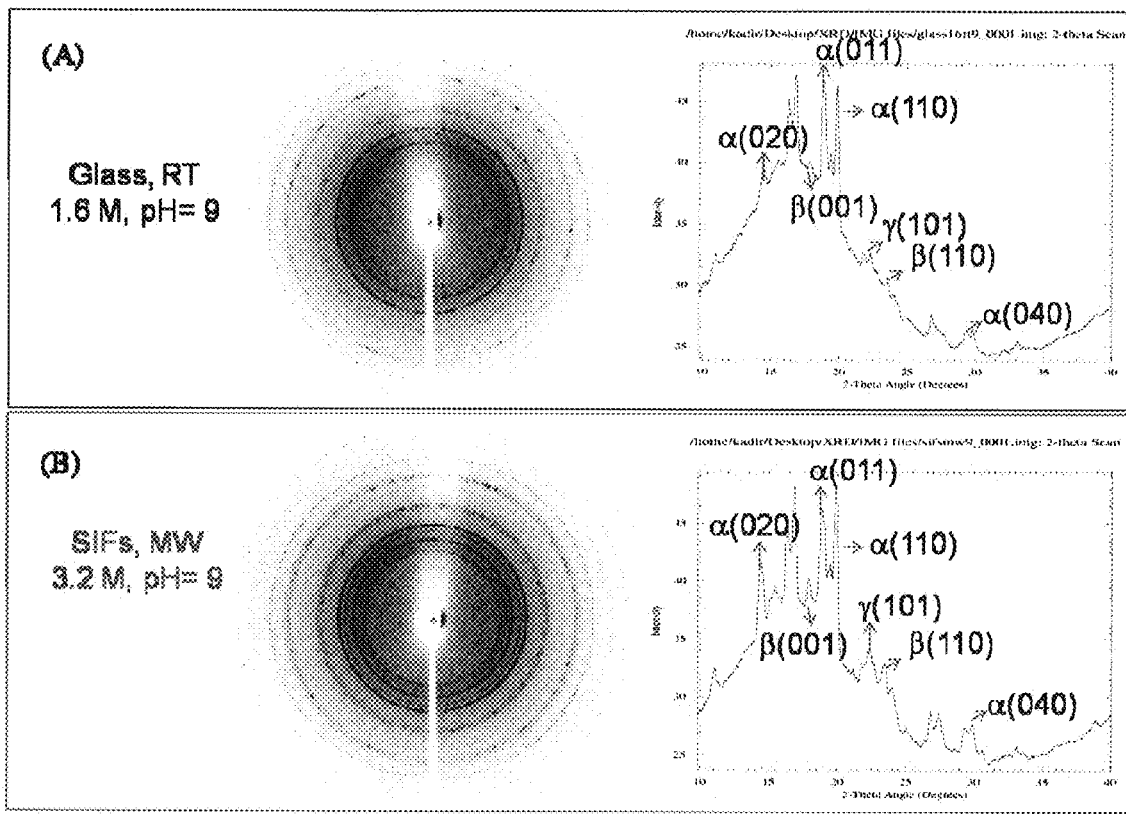
FIG. 20 shows experimental 2-D (Left) and 1-D (Right) patterns of glycine crystals grown from glycine solutions (A) 1.6 M pH=9 on glass at room temperature (RT) and (B) 3.2 M pH=9 on SIFs using microwave heating (MW).
Figure 21:
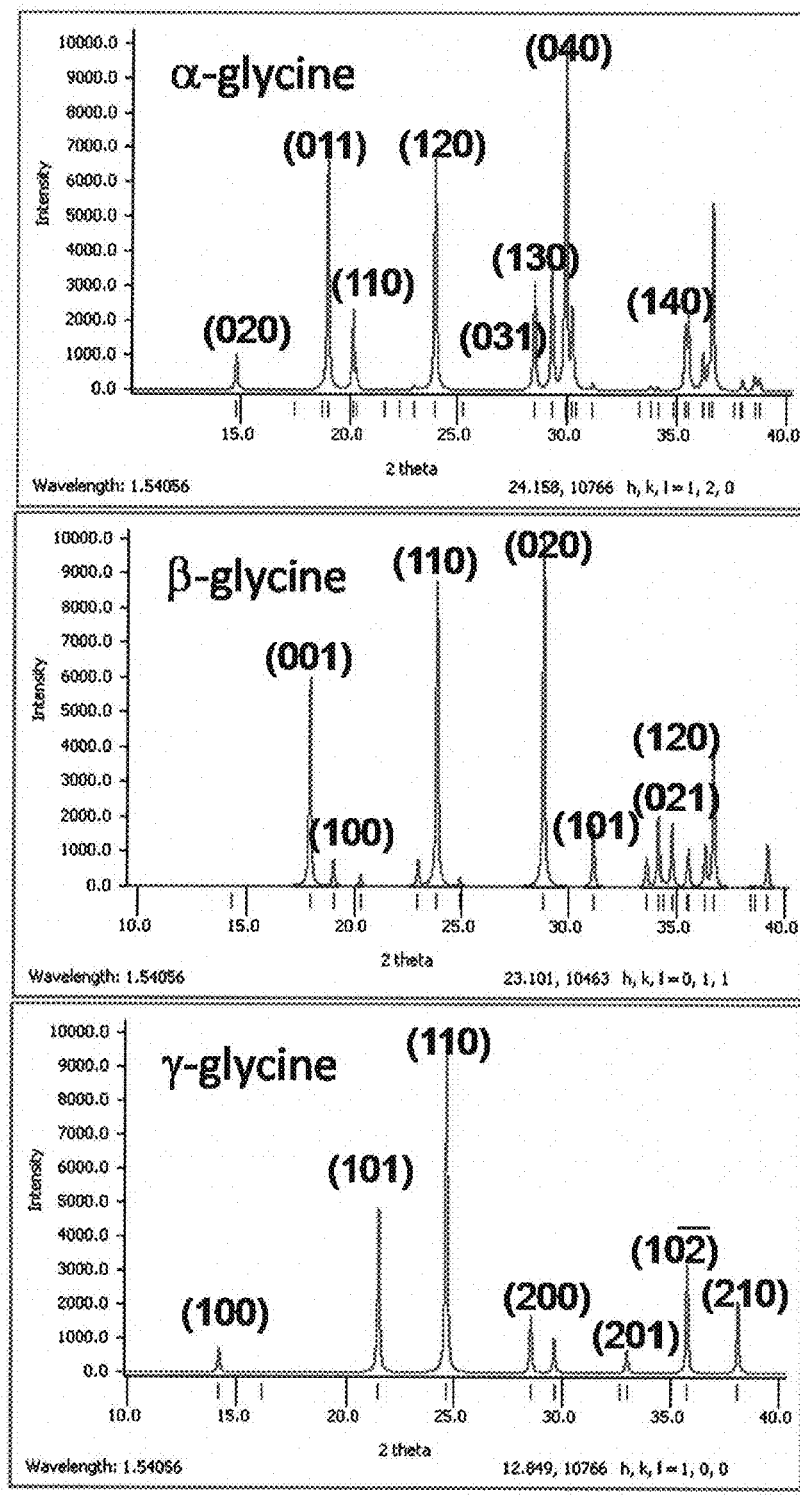
FIG. 21 shows simulated Powder X-Ray Diffraction patterns for α-, β- and γ-glycine crystals.

The collected 2-D XRD data (in .OSC format) was converted to ".IMG" and ".PS" formats using ADXV software (see Pinard et al. below). 1-D Intensity vs. $2\theta$ plots was obtained by fitting the ".IMG" files using FIT2D software (see Pinard et al. below). The polymorph reflections (e.g. $\alpha(020)$) were determined by comparing the peak locations in the $2\theta$ plots for the experimental (FIGS. 18-20) and simulated XRD patterns (FIG. 21).

Simulated XRD patterns for $\alpha$-, $\beta$-, and $\gamma$-glycine were generated using Mercury (Cambridge Crystallographic Data Center, Cambridge, United Kingdom, version 2.3). The crystallographic parameters for glycine crystals (CIF files) were obtained from published papers (Ferrari, E. S.; Davey, R. J.; Cross, W. I.; Gillon, A. L.; Towler, C. S. *Crystal Growth & Design* 2003, 3, 53-60; and Dawson, A.; Allan, D. R.; Belmonte, S. A.; Clark, S. J.; David, W. I. F.; McGregor, P. A.; Parsons, S.; Pulham, C. R.; Sawyer, L. *Crystal Growth & Design* 2005, 5, 1415-1427).

Figure 18:
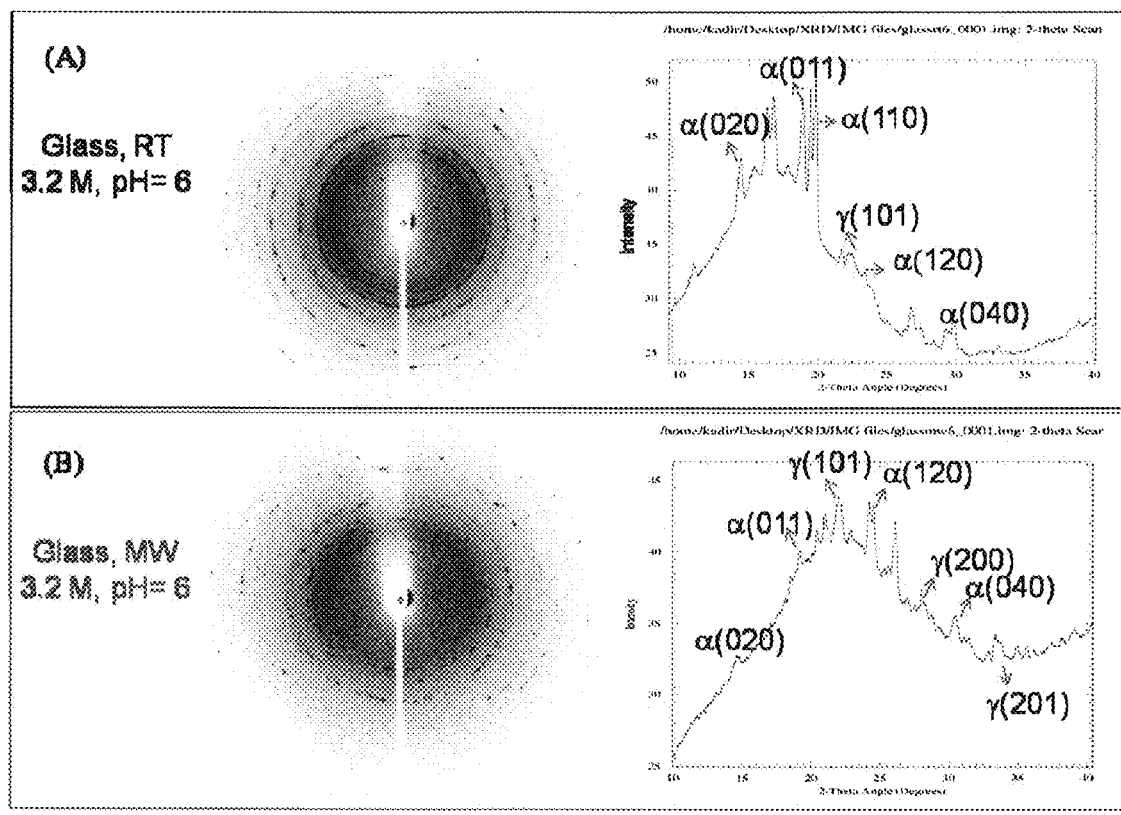
FIG. 18 shows experimental 2-D (Left) and 1-D (Right) Powder X-Ray Diffraction patterns of glycine crystals grown from glycine solutions 3.2 M pH=6 on glass (A) at room temperature (RT) and (B) using microwave heating (MW).
Figure 22:
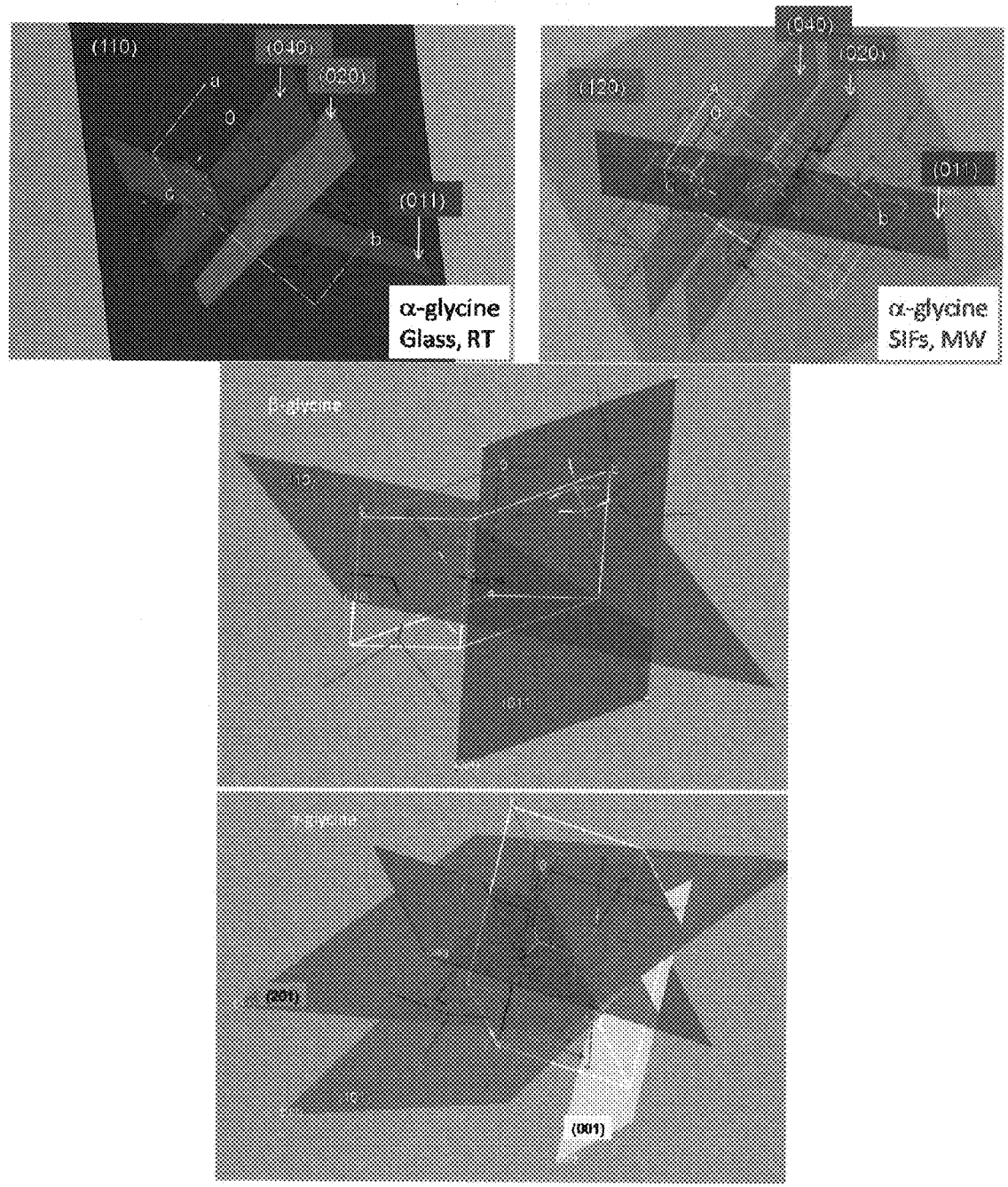
FIG. 22 shows simulated growth morphology of α-, β- and γ-glycine crystals, showing the selected crystal faces, which were observed in the experimental data.

Although optical microscopy and SEM images provide semi-quantitative information about the type of the glycine polymorphs due to the observable large size of crystals, the XRD data is more definitive. FIG. 18 shows the 2-D XRD data for crystals grown from a glycine solution (3.2 M, pH=6) on glass at room temperature and using microwave heating. The XRD data also corroborate that the observation made by microscopy that a mixture of $\alpha$- and $\gamma$-glycine was grown on glass at room temperature and using microwave heating. The intensity of reflections from glycine crystals grown on glass at room temperature was larger than those grown using microwave heating, which indicates the larger number of crystals grown at room temperature, as again evidenced by SEM and optical microscope images. It is important to note that identical glycine solution was used. In FIG. 18(A), the intensity of peaks for $\alpha(011)$, $\alpha(110)$ and $\alpha(020)$ are the largest indicating that glycine crystals are grown preferentially along these faces. FIG. 22 (Top-Left) shows the depiction of the morphology for $\alpha$-glycine crystals grown on glass at room temperature with these observed crystal faces. It is also interesting to note that bi-pyrimidal $\alpha$-glycine crystals are formed through hydrogen bonding that is strongest in the bc-plane (011) and ab-plane (110). In addition, XRD data (FIG. 18) shows that $\gamma$-glycine was preferentially grown along the (101) face on glass slides.

Figure 19:
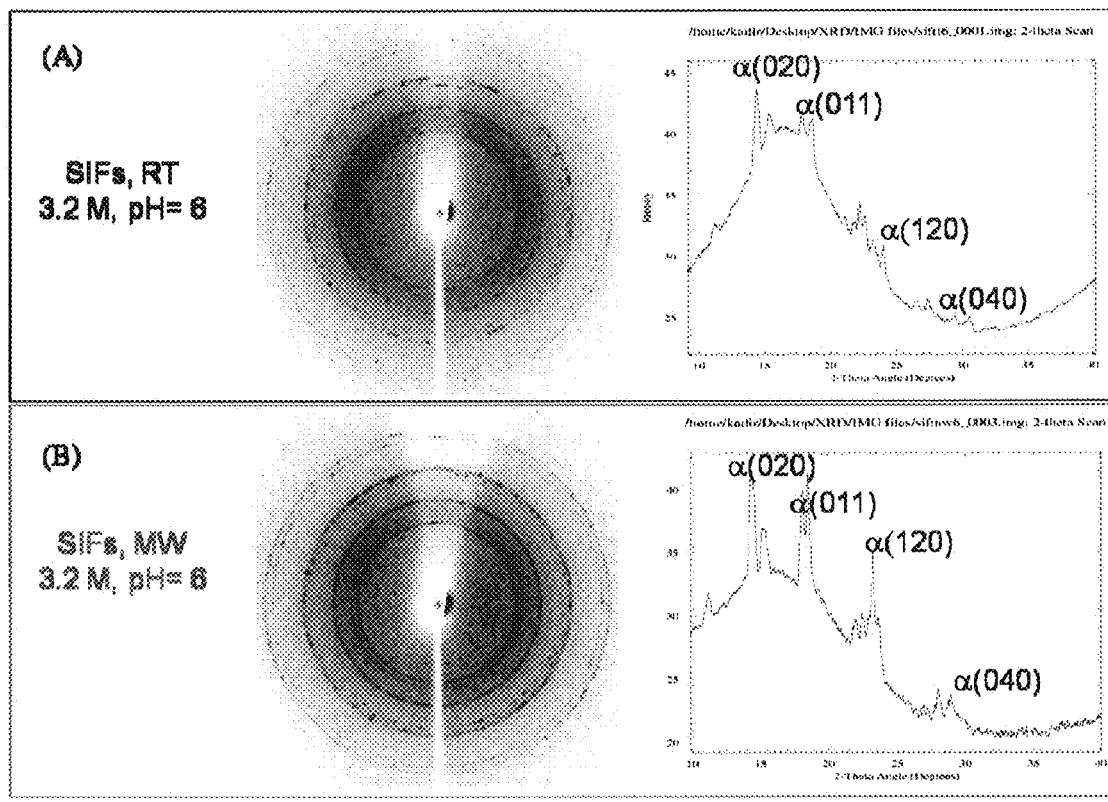
FIG. 19 shows experimental 2-D (Left) and 1-D (Right) X-Ray Diffraction patterns of glycine crystals grown from glycine solutions 3.2 M pH=6 on SIFs (A) at room temperature (RT) and (B) using microwave heating (MW).

FIG. 19 shows that only $\alpha$-glycine was grown on SIFs at room temperature and using microwave heating. It is important to remind that the crystallization on SIFs occurred much faster than on glass slides due to the presence of multiple silver nanoparticles within close proximity serving as nucleation/growth sites. This can be explained as in the following: once the initial glycine molecules are adsorbed onto silver nanoparticles through their amine groups, the subsequent glycine molecules are selectively assembled onto the first glycine molecules through the carboxylic acid groups (that is, Silver—[$NH_2$—COOH]—[$NH_2$—COOH]—[$NH_2$—COOH]—). The assembling of glycine molecules occurs faster under microwave heating due to the temperature gradient between the solution and the silver nanoparticles. Aslan, K.; Geddes, C. D. *Analyst* 2008, 133, 1469-80. In this regard, it is also thought that microwave heating lowers the activation energy for the hydrogen bonding between glycine molecules, effectively speeding up the crystallization process. On the other hand, the assembly of glycine molecules at room temperature takes up to 20 minutes due to the absence of the driving force (temperature gradient) for the rapid transfer of glycine molecules from the solution to the nucleation sites on the surface of the silver nanoparticles.

It is also interesting to note a notable difference between the $\alpha$-glycine crystals grown on glass at room temperature and on SIFs using microwave heating. As shown in the XRD data (FIGS. 18(A) and 19(B)), for $\alpha$-glycine crystals grown on glass a strong peak at ~20° corresponding to the (110) face and a weak peak at ~24° corresponding to the (120) face appears. Conversely, for $\alpha$-glycine crystals grown on SIFs, the intensity for the peak corresponding to the (120) face is stronger and the peak at ~20° corresponding to the (110) face is not present. The side-by-side comparison of the predicted $\alpha$-glycine crystals morphology for crystals grown on glass at room temperature and on SIFs using microwave heating is shown in FIG. 22—Top. Optical microscope and SEM images (FIGS. 10 and 16) show that the growth of $\alpha$-glycine crystals on glass occurred preferentially in the z-direction (into the solution; x-y is glass surface), where glycine molecules were assembled onto smaller number of nucleation sites on glass. In comparison, the growth of $\alpha$-glycine crystals on SIFs preferentially occurred in the x-y direction (on the surface), resulting in longer crystals due to the availability of large number of nucleation/growth sites (i.e., silver nanoparticles).

$\beta$-glycine crystals were also observed from some of the samples. FIG. 20 shows the XRD results for crystals grown from a 1.6 M, pH=9 glycine solution on glass at room temperature and from a 3.2 M, pH=9 glycine solution on SIFs using microwave heating. Once again, the reflections from $\alpha$-glycine and $\gamma$-glycine were dominant, and in both the samples $\beta(001)$ and $\beta(110)$ reflections were present. The presence of $\beta(001)$ and $\beta(110)$ reflections indicate that $\beta$-glycine crystals were grown as plates.

It is known that the heating of glycine solutions to higher temperatures results in the transformation of $\gamma$-form into $\alpha$- and $\beta$-forms. Lee, A. Y.; Lee, I. S.; Dettet, S. S.; Boerner, J.; Myerson, A. S. *Journal of the American Chemical Society* 2005, 127, 14982-14983. This is due to the fact that $\alpha$- and $\gamma$-glycine are enantiotropically related and such transformation occurs at high temperatures. See Lee et al above. The existence of the high energy $\beta$-form can be explained by the high supersaturation process resulted by rapid evaporation of water. See Lee et al above. The presence of $\gamma$-glycine on the surface after the crystallization process ended indicates the incomplete transformation of $\gamma$-glycine into $\alpha$- and $\beta$-forms. FIG. 22—Middle and FIG. 22—Bottom show the predicted $\beta$- and $\gamma$-glycine crystals morphology for crystals grown on glass at room temperature and on SIFs using microwave heating.

FIG. 18 shows experimental 2-D (Left) and 1-D (Right) Powder X-Ray Diffraction patterns of glycine crystals grown from glycine solutions 3.2 M pH=6 on glass (A) at room temperature (RT) and (B) using microwave heating (MW). The Greek letters on the 1-D plots indicate the type of glycine polymorph that the peak belongs, which was determined by comparing the simulated XRD pattern for all three polymorphs given in FIG. 21. The Miller indices corresponding to the peaks are also shown. The bell shape in the 1-D plot is due to the background signal as also observed in previous publications by others. Hamilton, B. D.; Hillmyer, M. A.; Ward, M. D. *Crystal Growth & Design* 2008, 8, 3368-3375; and Hamilton, B. D.; Weissbuch, I.; Lahav, M.; Hillmyer, M. A.; Ward, M. D. *Journal of the American Chemical Society* 2009, 131, 2588-2596.

FIG. 19 shows experimental 2-D (Left) and 1-D (Right) X-Ray Diffraction patterns of glycine crystals grown from glycine solutions 3.2 M pH=6 on SIFs (A) at room temperature (RT) and (B) using microwave heating (MW). The Greek letters on the 1-D plots indicate the type of glycine polymorph that the peak belongs, which was determined by comparing the simulated XRD patterns for all three polymorphs given in FIG. 21. The Miller indices corresponding to the peaks are also shown.

FIG. 20 shows experimental 2-D (Left) and 1-D (Right) patterns of glycine crystals grown from glycine solutions (A) 1.6 M pH=9 on glass at room temperature (RT) and (B) 3.2 M pH=9 on SIFs using microwave heating (MW). The Greek letters on the 1-D plots indicate the type of glycine polymorph that the peak belongs, which was determined by comparing the simulated XRD patterns for all three polymorphs given in FIG. 21. The Miller indices corresponding to the peaks are also shown.

FIG. 21 shows simulated Powder X-Ray Diffraction patterns for α-, β- and γ-glycine crystals. The Miller indices corresponding to the peaks are also shown.

FIG. 22 shows simulated growth morphology of α-, β- and γ-glycine crystals, showing the selected crystal faces, which were observed in the experimental data. Hydrogen bonds are indicated as dashed red lines.

This example is adapted from Pinard, M. A.; Aslan, K., Metal-Assisted and Microwave-Accelerated Evaporative Crystallization. *Cryst Growth Des* 2010, 10 (11), 4706-4709, the disclosure of which is incorporated herein by reference.

Example 2

L-Alanine is an important amino acid that plays a key role in the molecular structure of many proteins. Crystallized forms of this molecule are currently in high demand in chemical, pharmaceutics, and food industries. However, the traditional evaporative crystallization method takes up to several hours to complete, and does not always consistently yield usable crystals. Using the metal-assisted and microwave-accelerated evaporative crystallization (MA-MAEC) technique, larger and better-organized L-Alanine crystals were formed in a fraction of the time using room temperature crystallization. This technique may be applicable to organic molecules other than amino acids, and thus will be able to produce the large amount of molecular crystals desired by industries today.

L-Alanine is one of the most abundant amino acids used in the synthesis of proteins (see Yamada, K.; Sato, A.; Shimizu, T.; Yamazaki, T.; Yokoyama, S., L-alanine hydrochloride monohydrate. *Acta Crystallographica Section E-Structure Reports Online* 2008, 64, O806-U1439). Because of its structural simplicity and importance in protein construction, it is also a key molecule in crystallization research. Furthermore, because hydrogen bonding plays a large role in alanine's molecular structure, research concerning this particular amino acid can lead to a better understanding of the structural dimensions of macromolecules such as peptides and proteins (see Mohan, R.; Kumar, K. S.; Raghavalu, T.; Mathivanan, V.; Kovendhan, M.; Sivakumar, B.; Kumar, G. R.; Raj, S. G., Structural, optical, spectral and thermal studies of nonlinear optical pure and deuterated L-alanine single crystals. *Journal of Crystal Growth* 2008, 310, (6), 1182-1186). A number of studies have been conducted on the properties of crystallized L-Alanine, including studies about its vibrational spectra (see Machida, K. K., A.; Saito, Y.; Uno, T., Polarized Raman spectra and intermolecular potential of L-alanine crystal. *Spectrochim. Acta, Part A* 1978, 34, 909-914), morphology (see Lechuga-Ballesteros, D. R.-H., N., Effects of molecular structure and growth kinetics on the morphology of L-alanine crystals. *Int. J. Pharm* 1995, 115, 151-160), and thermal properties (see Mohan, R.; Kumar, K. S.; Raghavalu, T.; Mathivanan, V.; Kovendhan, M.; Sivakumar, B.; Kumar, G. R.; Raj, S. G., Structural, optical, spectral and thermal studies of nonlinear optical pure and deuterated L-alanine single crystals. *Journal of Crystal Growth* 2008, 310, (6), 1182-1186). However, a majority of these studies utilized the traditional room temperature evaporative crystallization method, which can take up to several days to complete.

In this Example, the application of metal-assisted and microwave-accelerated evaporative crystallization (MA-MAEC) to rapid crystallization of L-alanine, is used. The MA-MAEC technique is based on the combined use of microwave heating (for speeding up the crystallization process) and plasmonic nanostructures (silver island films, SIFs, as selective nucleation sites) for L-alanine crystal growth. The MA-MAEC technique is a promising new method for rapid molecular crystallization that significantly decreases the amount of time required for complete evaporation and crystallization to occur.

The effect of using SIFs and evaporative crystallization conditions (room temperature and microwave-accelerated) on the time of crystallization and type of crystals of L-alanine were studied. Table 2 below summarizes the results for the crystallization of L-Alanine at room temperature and using the MA-MAEC technique.

TABLE 2

Summary of results for the crystallization of 20 μl L-alanine from 2.70M solution on glass slides and silver island films (SIFs) at room temperature and using MA-MAEC technique. N = 5 samples.

|  | Glass | SIFs | Type of Crystal |
|---|---|---|---|
| Room Temperature | 50 ± 3 min | 41 ± 13 min | α |
| Microwave Power Level 1 | 6.5 ± 1 min | 7 ± 1 min | α |
| Microwave Power Level 5 | 41 ± 3 sec | 45 ± 6 sec | α |
| Microwave Power Level 10 | 38 ± 2 sec | 22 ± 3 sec | α |

For a fixed volume (20 μl) and concentration (2.70 M, pH=5.3) of L-Alanine (minimum of 5 samples were used), the crystallization process on blank glass slides and SIFs took 50±3 minutes and 41±13 minutes on average at room temperature, respectively. Complete L-Alanine crystallization required 38 seconds to 6.5 minutes when using the microwave-accelerated evaporative crystallization (MAEC) technique on blank glass slides. Observable crystals formed on 25 of 31 blank glass slides, which is consistent with previously published results for L-glycine. Average crystallization time decreased as the microwave power level was increased when using the MA-MAEC technique. For example, crystallization of L-alanine was completed in only 22 seconds on SIFs when using the MA-MAEC technique at microwave power level 10 and in 7 minutes on SIFs at microwave power level 1. It is also important to note that all SIFs surfaces yielded observable L-alanine crystals. The α-form of L-Alanine crystals was observed by optical microscopy in all samples in this Example, which is similar to observations made by other groups (see Lechuga-Ballesteros, D. R.-H., N., Effects of molecular structure and growth kinetics on the morphology of L-alanine crystals. *Int. J. Pharm* 1995, 115, 151-160, and Koyama, M.; Shiraishi, M.; Sasaki, K.; Kon-no, K., Preparation of L-Alanine Crystals Containing Gold Nanoparticles. *Journal of Dispersion Science and Technology* 2008, 29, (9), 1266-1271).

Figure 4:
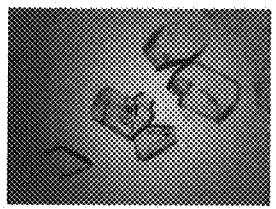
FIG. 4 shows optical images of L-Alanine crystals formed on blank glass slides and SIFs from 2.70 M solution at room temperature and using MA-MAEC technique. All images were taken with the same optical setup.
Figure 4:
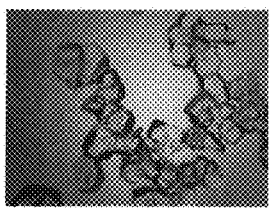
Figure 4:
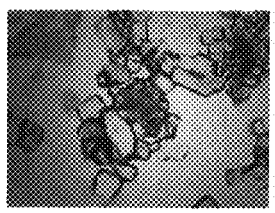
Figure 4:
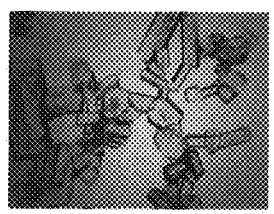
Figure 4:
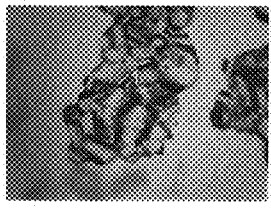
Figure 4:
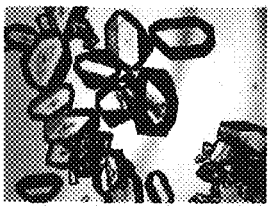
Figure 4:
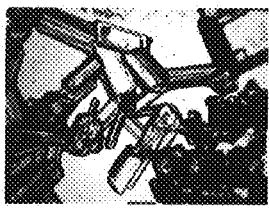
Figure 4:
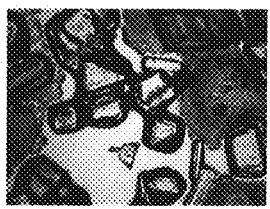

FIG. 4 shows the visual comparison of L-alanine crystals formed using room temperature and MA-MAEC techniques on both blank glass slides and on SIFs. Crystals grown using the MA-MAEC technique were consistently larger than those grown using room temperature crystallization. Crystal size ranged from 110 to 589 μm on blank glass slides and from 141 to 581 μm on SIFs after complete evaporation. Crystals were believed to have stopped growing after complete evaporation of the aqueous solution because of a decrease in supersaturation of the solution (see Koyama, M.; Shiraishi, M.; Sasaki, K.; Kon-no, K., Preparation of L-Alanine Crystals Containing Gold Nanoparticles. *Journal of Dispersion Science and Technology* 2008, 29, (9), 1266-1271). Consistent with previous research, all α-crystals had the largest face zone and were elongated along what was believed to be the c-axis (see Lechuga-Ballesteros, D. R.-H., N., Effects of molecular structure and growth kinetics on the morphology of L-alanine crystals. *Int. J. Pharm* 1995, 115, 151-160).

As described in Pinard, M. A.; Aslan, K., Metal-Assisted and Microwave-Accelerated Evaporative Crystallization. *Cryst Growth Des* 2010, 10 (11), 4706-4709, these observations were attributed to the fact that SIFs serve as selective nucleation sites for L-alanine crystal growth and as a microwave-transparent medium for the creation of thermal gradient between the warmer solution and the silver nanostructures that remain at room temperature after microwave heating. The microwave heating allows for the significant reduction in the time of crystallization process. It is well known that amine groups have affinity towards plasmonic nanoparticles, such as silver in particular (see Myerson, A. S.; Lee, A. Y.; Lee, I. S.; Dettet, S. S.; Boerner, J., Crystallization on confined engineered surfaces: A method to control crystal size and generate different polymorphs. *Journal of the American Chemical Society* 2005, 127, (43), 14982-14983). Therefore, it is thought that the amine groups of L-alanine assemble onto silver nanostructures, becoming probable nucleation sites for the growth of crystals. This hypothesis was tested by comparison of crystal growth on blank glass slides and SIFs. Compared to L-alanine crystals formed on blank glass slides at room temperature, crystals grown on SIFs were more abundant and had fewer imperfections. They also appeared to be more homogeneous in size than crystals grown on glass slides, where larger variation in the size of the crystals was observed.

It is also important to note that the size distribution of the crystals grown on blank glass slides and SIFs using microwave power level 1 was homogeneous as compared to heterogeneous size distribution observed using microwave power levels 5 and 10. This is attributed to the excess microwave heating of the solution and the crystals formed during microwave heating (at power level 5 and 10). It is thought that excess microwave heating affects the crystal nucleation and growth by further increasing the rate of these processes.

Figure 5:
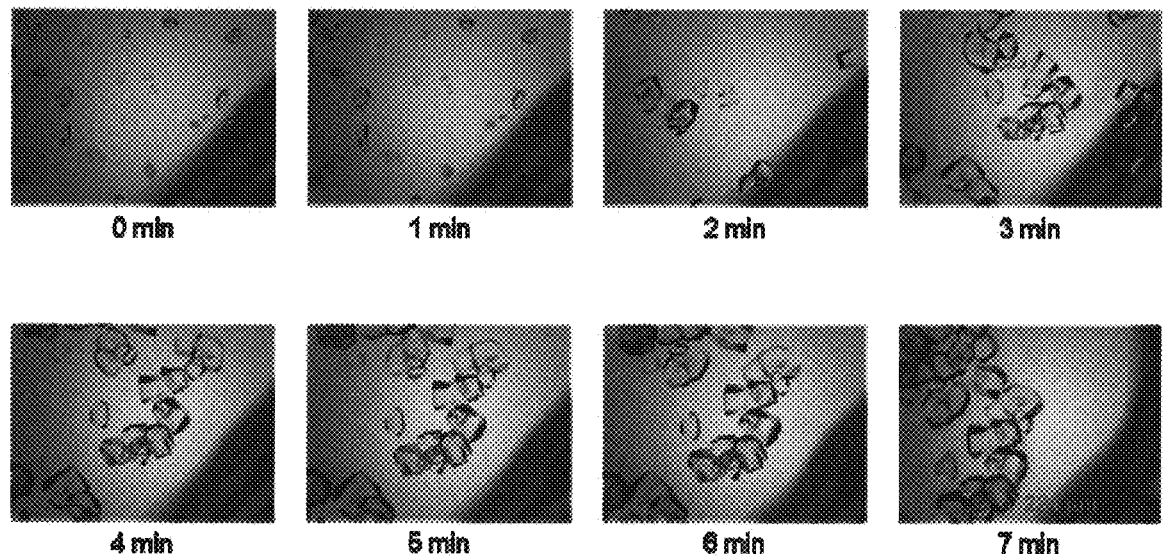
FIG. 5 shows the time progression of the growth of L-alanine crystals on blank glass slides using MAEC technique at microwave power level 1.

In order to better understand the crystallization process during room temperature and microwave heating evaporation, optical images of the solution and the growing crystals on blank glass slides and SIFs were taken at time intervals as indicated in FIGS. 5, 6 and 23-28. In all these experiments, microwave heating was stopped for a brief period of time (~10 sec) to collect optical images. FIG. 5 (Glass_MW_PL1) shows the timed crystal growth progression on glass slides at microwave power level 1. Smaller crystals appeared by the time of the first image (t=0 min) was taken. The crystal growth is clearly seen in the subsequent images, where the crystals seemed to grow to their final size at 4-7 min. These images also show that the crystal movement (t=0 to t=6 min) in solution, after which they rest in their final places after the complete evaporation of the solvent (at t=7 min). Similar observations were also made for crystals grown on glass slides using microwave power level 5 and 10 and room temperature (see FIGS. 23-25).

Figure 6:
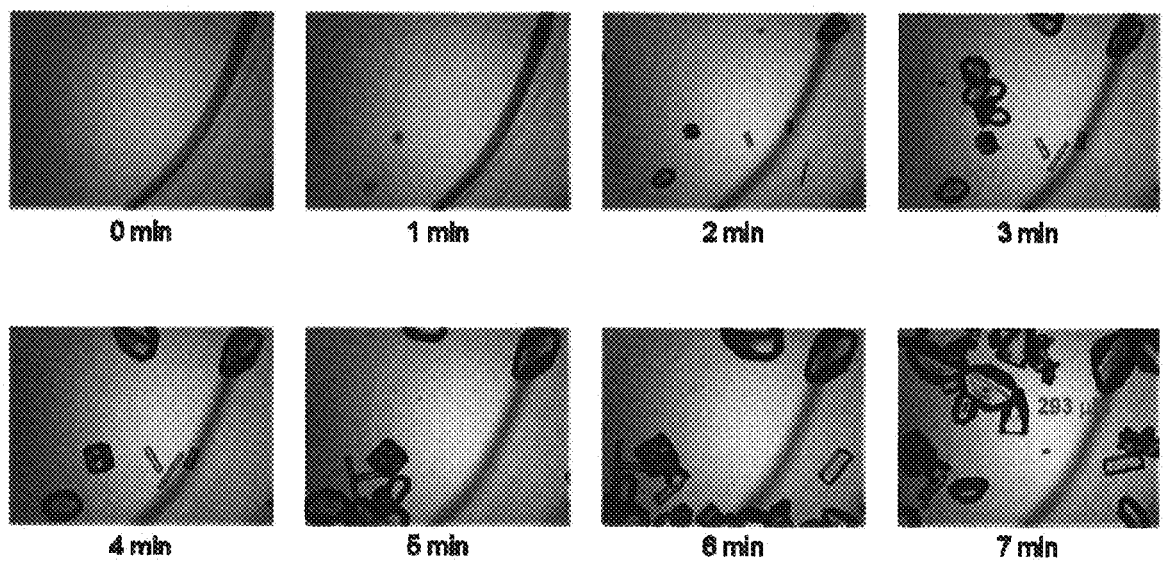
FIG. 6 shows the time progression of the growth of L-alanine crystals on SIFs using MA-MAEC technique at microwave power level 1.

FIG. 6 (SIF_MW_PL1) shows the timed crystal growth progression on SIFs using microwave power level 1. Crystals first started to appear on SIFs around 2 min of microwave heating, after which significant growth was observed until complete evaporation at t=7 min. At microwave power levels 1 and 5, significant improvement of the growth of crystals was observed on SIFs compared to glass slides. These crystals were much more abundant and of better quality than those grown using the MAEC technique on glass, which were imperfect and scarce in quantity. Crystal growth occurred on all SIFs samples of each microwave heating condition, and took only 22 seconds to 7 minutes for complete evaporation (microwave power level 1 and 10, respectively), proving that the same crystals can be grown using the MA-MAEC technique over 10-fold faster than the traditional evaporative crystallization method. The abundance of L-alanine crystals formed using the MA-MAEC method can be explained by the presence of silver nanoparticles on the surface. SIFs served as nucleation sites that allowed for the growth of crystals in large quantities (see Pinard, M. A.; Aslan, K., Metal-Assisted and Microwave-Accelerated Evaporative Crystallization. *Cryst Growth Des* 2010, 10, (11), 4706-4709). In comparison, the nucleation and growth of L-alanine crystals were random in nature due to the lack of functional surface groups on glass slides.

It is also important to note that when applying microwave heating to the L-alanine solution on both glass slides and SIFs, crystal organization improved when the microwave was stopped and started multiple times for imaging purposes, as compared to uninterrupted microwave heating of the same amount of time. This might be explained by the high amount of microwave energy being absorbed by the L-alanine solution in a short period of time. The amount of energy present may have been higher than required for crystal growth, and thus may have prevented the crystals from their normal growth.

Figure 7:
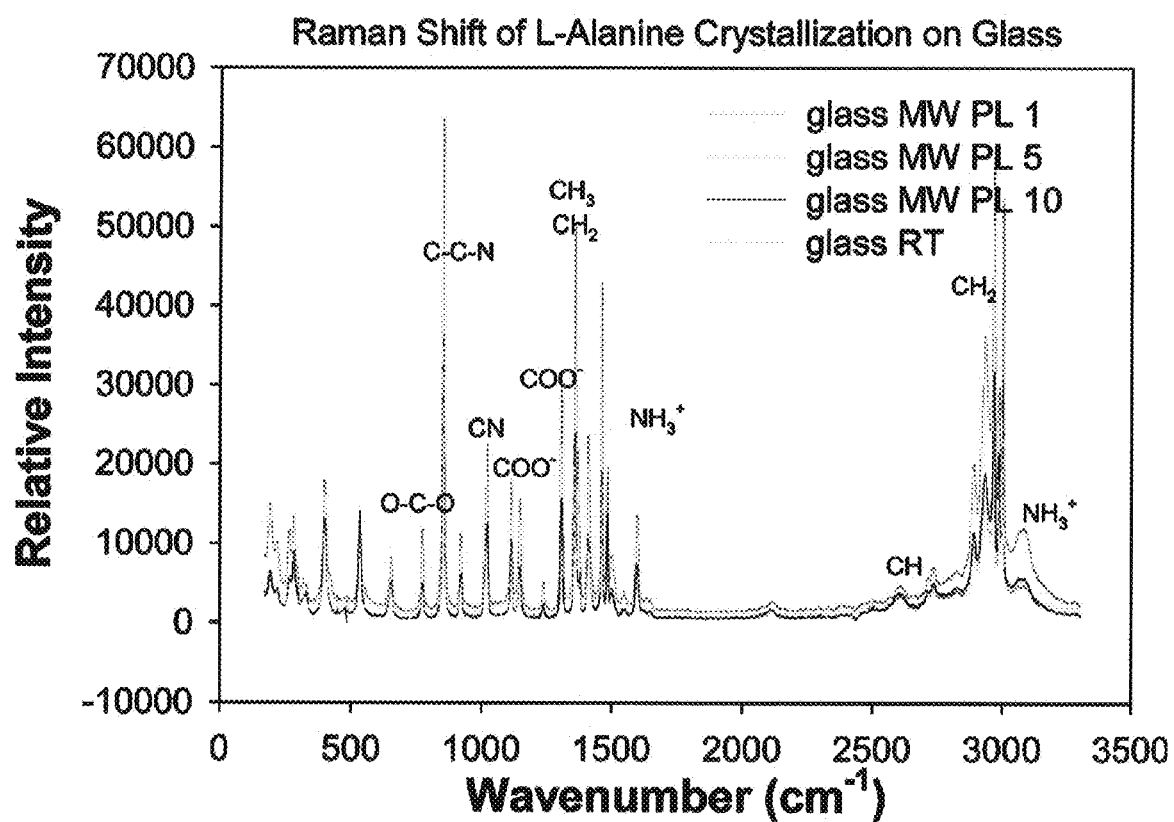
FIG. 7 shows a Raman spectrum of L-alanine crystallized on blank glass slides at room temperature and using the MA-MAEC technique (notation of functional groups at peaks signifies presence of functional group at the indicated wavelength).
Figure 8:
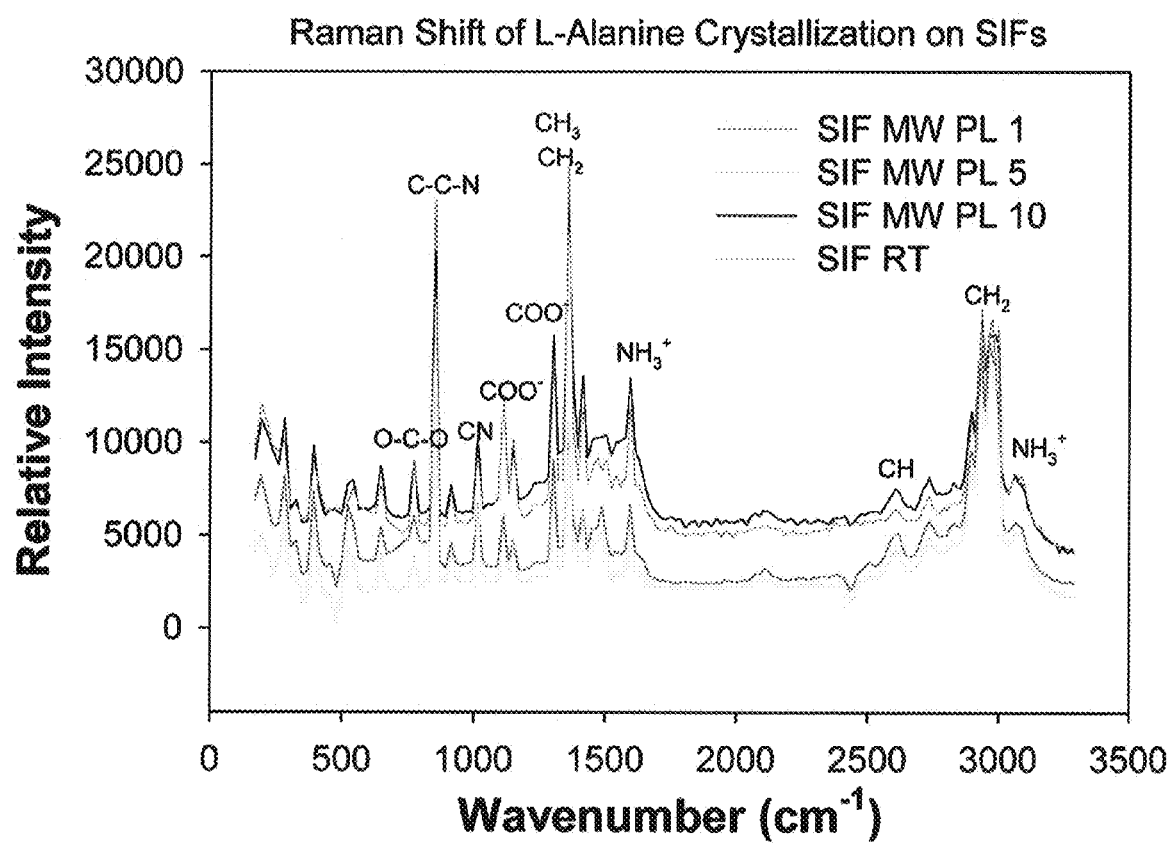
FIG. 8 shows a Raman spectrum of L-alanine crystallized on SIFs at room temperature and using the MA-MAEC technique (notation of functional groups at peaks signifies presence of functional group at the indicated wavelength).

FIGS. 7 and 8 shows the Raman spectra of L-alanine crystals grown on glass slides and SIFs at room temperature and using the MA-MAEC technique. Observable peaks appear in the same locations as those in previously published results (see Mohan, R.; Kumar, K. S.; Raghavalu, T.; Mathivanan, V.; Kovendhan, M.; Sivakumar, B.; Kumar, G. R.; Raj, S. G., Structural, optical, spectral and thermal studies of nonlinear optical pure and deuterated L-alanine single crystals. *Journal of Crystal Growth* 2008, 310, (6), 1182-1186) for L-alanine grown on both glass and SIFs. This indicates that the crystals produced in this Example possess similar vibrational properties to other L-alanine crystals, and thus can be deemed the type of L-alanine crystals typically formed through room temperature evaporation from an aqueous L-alanine solution. Furthermore, since the Raman peaks are observed in identical locations on glass slides and SIFs, it can be concluded that the use of microwave heating and SIFs accelerate the crystallization process without altering the structural and vibrational properties of the crystals grown on them.

In summary, the results of this Example prove that the MA-MAEC technique is a highly effective method for rapid crystallization of L-alanine. Crystals produced using microwave-heating were larger in size than those grown at room temperature for both SIFs and glass slides, and were produced at a rate over 10-fold faster than that of the room temperature method. The presence of silver nanostructures on surfaces allowed for more selective nucleation sites than on blank glass slides, and therefore the simultaneous growth of more crystals was able to occur. Furthermore, the majority of crystals grown on SIFs was of better quality and appeared with fewer imperfections than those grown on glass. This Example demonstrates that the use of the MA-MAEC technique increases the efficiency of the crystallization of amino acids.

Supporting Information: The additional images of L-alanine crystals and experimental details are discussed below.

Materials

Silver nitrate was purchased from Spectrum Chemical MFG Corp. Sodium hydroxide, ammonium hydroxide, D-glucose, and L-Alanine were purchased from Sigma-Aldrich. All chemicals were used as received.

Methods

Preparation of Silver Island Films. Silver island films were deposited onto glass slides (Corning). $AgNO_3$ was precipitated by the addition of 5% NaOH, then quickly redissolved by the addition of $NH_4OH$. The solution was then cooled to 5° C. and blank glass slides were immersed in the solution for two minutes. D-glucose was added and the slides were removed once they were coated with a green color, after 5-7 minutes.

Preparation of L-Alanine Solution. A 2.70 M solution of L-alanine was prepared by dissolving appropriate amounts of L-alanine in double-distilled water (Millipore), then heated to 60° C. for up to 15 minutes, or until the solution appeared colorless and transparent. The pH of the prepared solution was slightly acidic at 5.3 (isoelectric point=6) and was used in all experiments without changing the pH. The solution was stored in a 20 mL glass vial (Corning) at room temperature in between uses, and was heated to 60° C. for 10 minutes before each use.

Crystallization of L-Alanine. L-Alanine was deposited in 20 μL drops onto blank glass slides (Corning) and SIFs, and was observed for crystallization at room temperature and MA-MAEC. Room temperature crystallization was carried out on an open laboratory bench without interference. The MAEC technique was performed in a conventional microwave oven (Frigidaire, 900 W) at microwave power levels 1, 5, and 10.

Timed images of growing crystals were recorded with a Swift Digital M10L Monocular Microscope (Swift). The Raman spectra of L-alanine crystals were observed using a Raman spectrometer system (i-Raman from BW Tek, Inc. DE).

Figure 23:
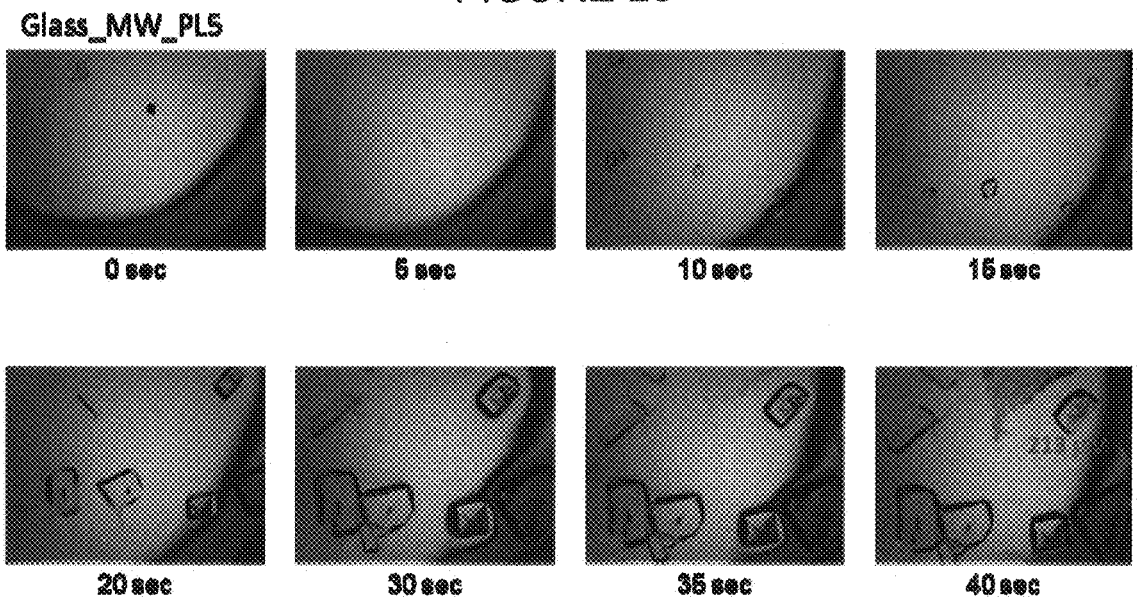
FIG. 23 shows the time progression of the growth of L-alanine crystals on blank glass slides using MAEC technique at microwave power level 5.

FIG. 23 shows the time progression of the growth of L-alanine crystals on blank glass slides using MAEC technique at microwave power level 5. The actual length of the crystals is ×4 of the lengths shown in the figure.

Figure 24:
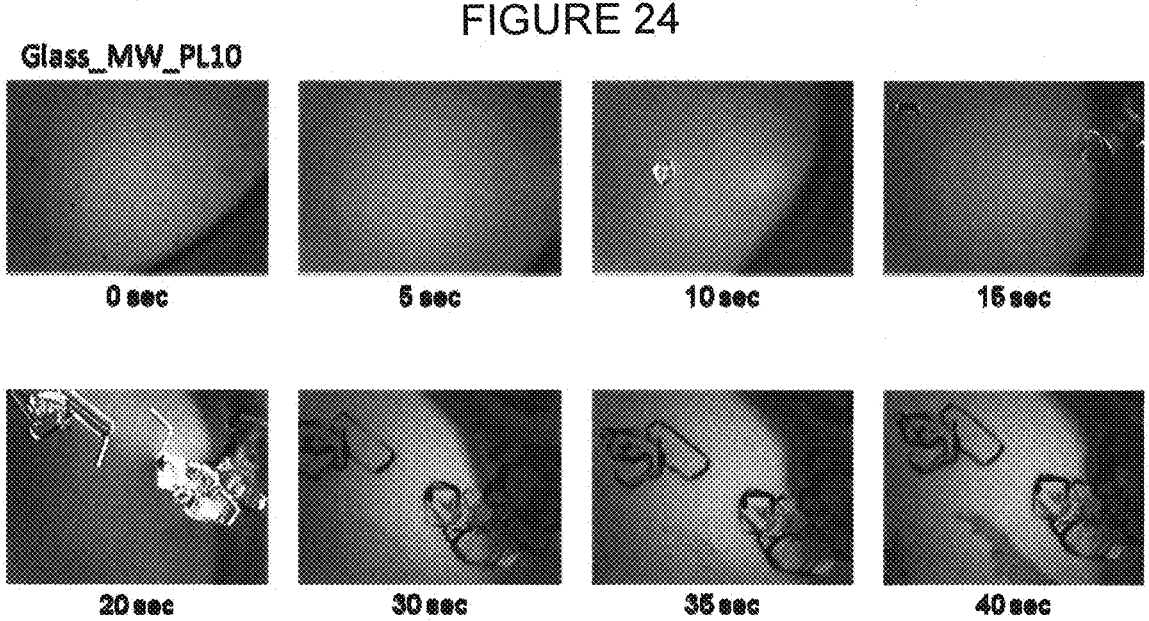
FIG. 24 shows the time progression of the growth of L-alanine crystals on blank glass slides using MAEC technique at microwave power level 10.

FIG. 24 shows the time progression of the growth of L-alanine crystals on blank glass slides using MAEC technique at microwave power level 10. The actual length of the crystals is ×4 of the lengths shown in the figure.

Figure 25:
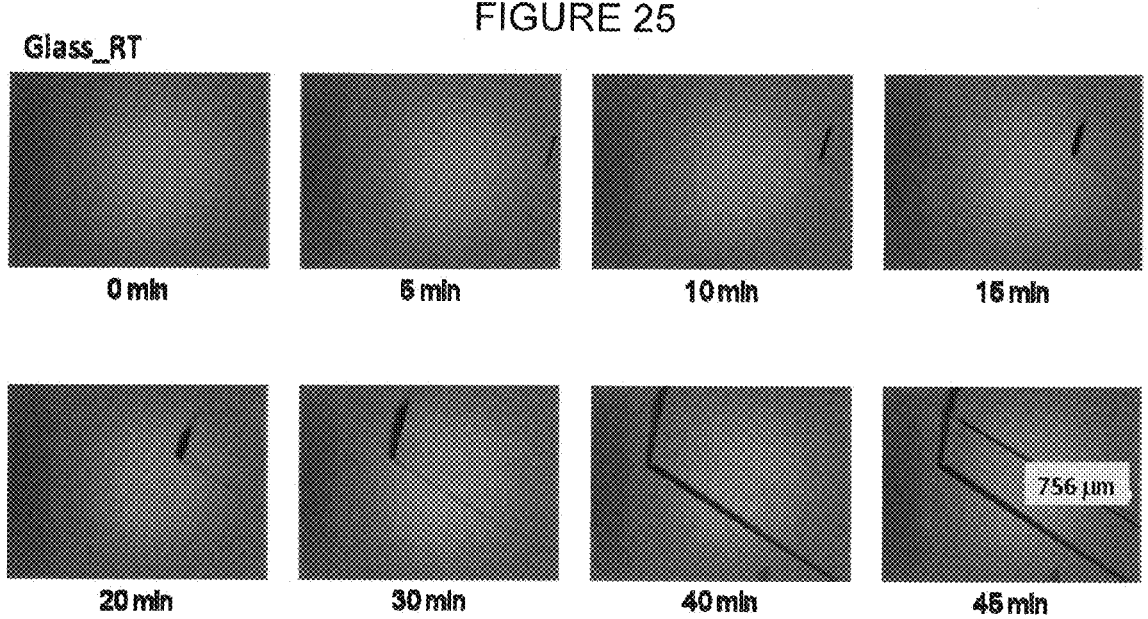
FIG. 25 shows the time progression of the growth of L-alanine crystals on blank glass slides at room temperature.

FIG. 25 shows the time progression of the growth of L-alanine crystals on blank glass slides at room temperature. The actual length of the crystals is ×4 of the lengths shown in the figure.

Figure 26:
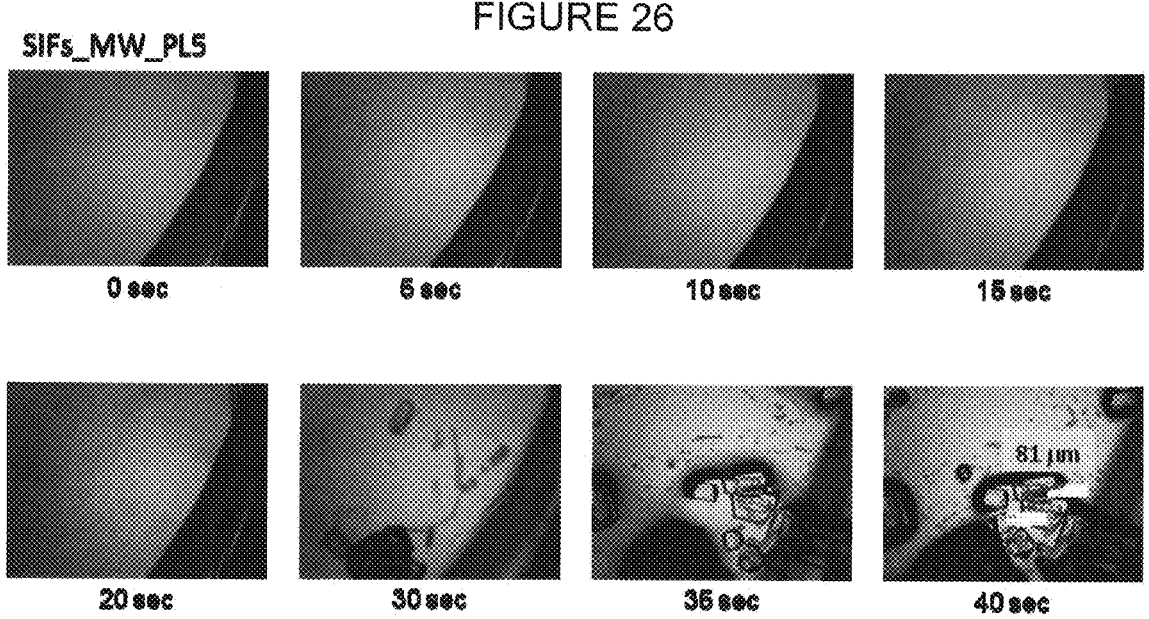
FIG. 26 shows the time progression of the growth of L-alanine crystals on SIFs using MA-MAEC technique at microwave power level 5.

FIG. 26 shows the time progression of the growth of L-alanine crystals on SIFs using MA-MAEC technique at microwave power level 5. The actual length of the crystals is ×4 of the lengths shown in the figure.

Figure 27:
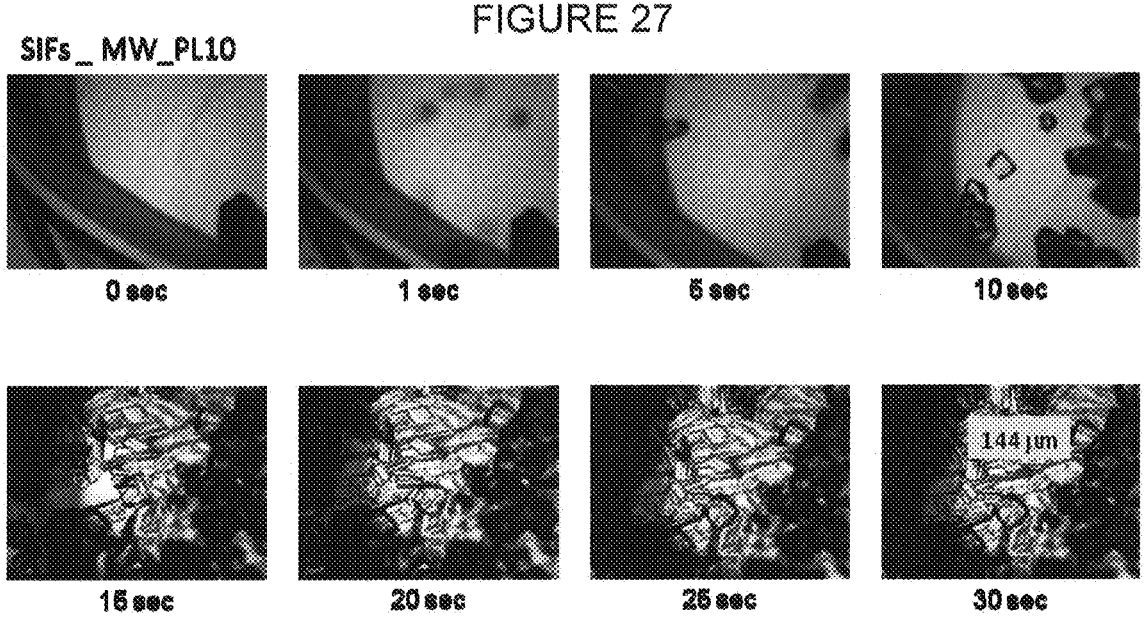
FIG. 27 shows the time progression of the growth of L-alanine crystals on SIFs using MA-MAEC technique at microwave power level 10.

FIG. 27 shows the time progression of the growth of L-alanine crystals on SIFs using MA-MAEC technique at microwave power level 10. The actual length of the crystals is ×4 of the lengths shown in the figure.

Figure 28:
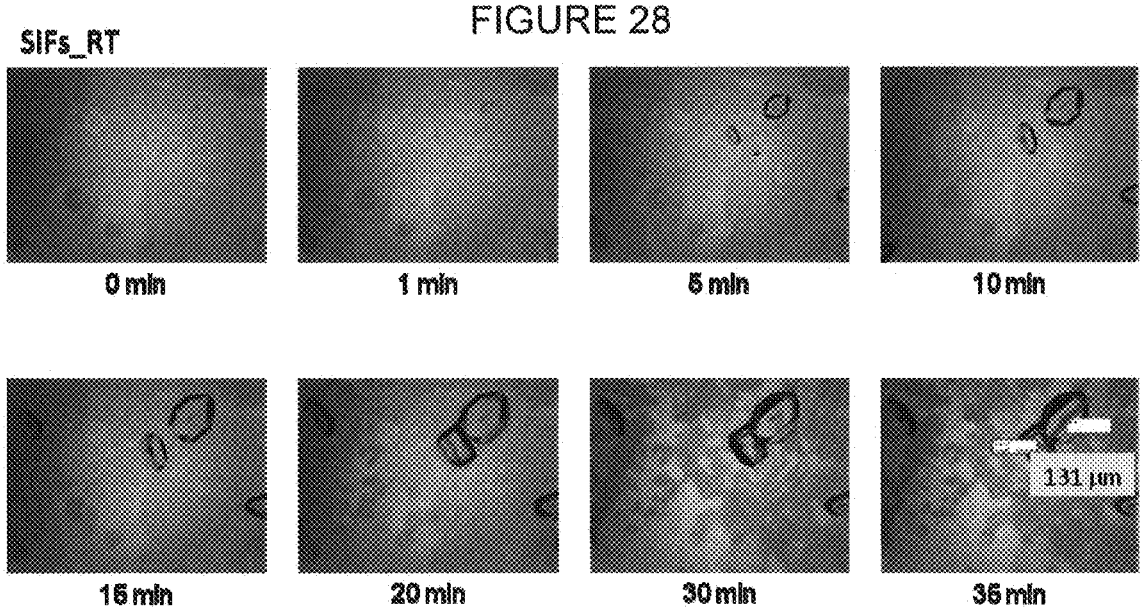
FIG. 28 shows the time progression of the growth of L-alanine crystals on SIFs at room temperature.

FIG. 28 shows the time progression of the growth of L-alanine crystals on SIFs at room temperature. The actual length of the crystals is ×4 of the lengths shown in the figure.

FIG. 29 shows a powder X-ray diffraction pattern of L-alanine crystals grown in this example.

This example is adapted from Alabanza, A. M.; Aslan, K., Metal-Assisted and Microwave-Accelerated Evaporative Crystallization: Application to L-Alanine. *Cryst Growth Des* 2011, 11 (10), 4300-4304, the disclosure of which is incorporated herein by reference.

While the invention has been described in detail and with reference to specific embodiments thereof, it will be apparent to one skilled in the art that various changes can be made without departing from the spirit and scope thereof.

What is claimed is:

1. A method for rapid crystallization of functional group-containing molecules selected from the group consisting of amino acids, drug molecules, proteins and DNA/peptides, the method comprising
    (A) providing at least one metal or metal oxide in particulate or thin film form to provide (a) selective nucleation sites for crystallization of the functional group-containing molecules due to interactions of their functional groups and metal surfaces or engineered metal surfaces and (b) a microwave-transparent medium to create a thermal gradient between the metal surfaces or engineered metal surfaces and a warmer solution containing functional group-containing molecules to be crystallized, and
    (B) conducting microwave heating to cause the functional group-containing molecules to be crystallized.

2. The method according to claim 1, wherein the at least one metal or metal oxide in particulate or thin film form is silver, gold, copper, aluminum, zinc, chromium, palladium, nickel, rhodium, iron, platinum, tin, gallium, indium, cadmium, cobalt, manganese, ruthenium, or an oxide thereof.

3. The method according to claim 1, wherein the at least one metal or metal oxide in particulate or thin film form is deposited onto a glass slide, polymeric material, paper or ceramic in a patterned fashion.

4. The method according to claim 1, wherein the at least one metal or metal oxide in particulate or thin film form is deposited onto a glass slide, polymeric material, paper or ceramic in a random fashion.

5. The method according to claim 3, wherein the polymeric material is selected from the group consisting of polyamide, polycarbonate, polyester, polyetherimide, polyimide, polynitrocellulose, polyethylene, polypropylene, poly(ethylenevinylacetate), poly-2-pentene, polyphenylene oxide, polyphenylene sulfide, polysulfone, and polystyrene.

6. The method according to claim 4, wherein the polymeric material is selected from the group consisting of polyamide, polycarbonate, polyester, polyetherimide, polyimide, polynitrocellulose, polyethylene, polypropylene, poly(ethylenevinylacetate), poly-2-pentene, polyphenylene oxide, polyphenylene sulfide, polysulfone, and polystyrene.

7. The method according to claim 1, wherein the metal surfaces or engineered metal surfaces comprise a single metal or metal oxide.

8. The method according to claim 1, wherein the metal surfaces or engineered metal surfaces comprise any combination of metals or metal oxides.

9. The method according to claim 1, wherein the at least one metal or metal oxide is in particulate form and has a particle size in a range of 2 nanometers to 2000 nanometers.

10. The method according to claim 1, wherein the at least one metal or metal oxide is in thin film form and has a thin film thickness in a range of 10 nanometers to 2000 nanometers.

11. The method according to claim 1, further comprising metal surfaces modified with a) compounds containing i) amine or thiol head groups, ii) 3 to 16 methylene groups, and iii) functional end groups selected from the group consisting of amine, carboxyl, hydroxyl, and ethyl, or b) compounds containing i) amine or thiol head groups and ii) DNA or peptide or polynucleic acid or any single amino acid as functional end groups.

12. The method according to claim 1, wherein the microwave heating is at a microwave frequency selected from microwave frequencies of 0.3 to 30 GHz using microwave power range 1 W-30000 W.

13. The method according to claim 12, wherein the microwave frequency is 2.45 GHz.

14. The method according to claim 1, wherein the amino acids are selected from the group consisting of isoleucine, alanine, leucine, asparagine, lysine, aspartic acid, methionine, cysteine, phenylalanine, glutamic acid, threonine, glutamine, tryptophan, glycine, valine, proline, selenocysteine, serine, tyrosine, arginine, histidine, ornithine, and taurine.

15. The method according to claim 1, wherein the amino acids are selected from the group consisting of glycine, alanine, arginine, and glutamic acid.

16. The method according to claim 1, wherein the drug molecules are selected from the group consisting of acetaminophen and ranitidine.

17. The method according to claim 1, wherein the proteins are selected from the group consisting of proteins found in humans and animals at their healthy and diseased states.

18. The method according to claim 1, wherein the DNA and peptides are selected from the group consisting of DNA and peptides found in humans and animals at their healthy and diseased states.

19. The method according to claim 1, wherein the functional groups are selected from the group consisting of amine, thiol, ethyl, and hydroxyl.

20. The method according to claim 1, wherein the metal surfaces or engineered metal surfaces remain at room temperature after microwave heating.

* * * * *